(12) United States Patent
Bodily

(10) Patent No.: US 7,742,880 B2
(45) Date of Patent: Jun. 22, 2010

(54) APPARATUS, SYSTEM, AND METHOD FOR BROAD SPECTRUM CHEMICAL DETECTION

(75) Inventor: Gary Bodily, Logan, UT (US)

(73) Assignee: Seer Technology, Inc., Salt Lake City, UT (US)

( * ) Notice: Subject to any disclaimer, the term of this patent is extended or adjusted under 35 U.S.C. 154(b) by 25 days.

(21) Appl. No.: 11/765,388

(22) Filed: Jun. 19, 2007

(65) Prior Publication Data

US 2008/0010029 A1    Jan. 10, 2008

Related U.S. Application Data

(60) Provisional application No. 60/805,309, filed on Jun. 20, 2006.

(51) Int. Cl.
*G01N 9/32*     (2006.01)

(52) U.S. Cl. ................ 702/32; 702/30; 702/182; 702/183

(58) Field of Classification Search ............ 702/19, 702/20, 32, 33, 179, 182, 183; 210/198.2; 424/168.1; 435/6; 436/86; 506/12
See application file for complete search history.

(56) References Cited

U.S. PATENT DOCUMENTS

| | | | |
|---|---|---|---|
| 3,062,037 A | 11/1962 | Donner et al. | |
| 3,165,146 A | 1/1965 | Smith et al. | |
| 3,174,326 A | 3/1965 | Carle et al. | |
| 3,250,395 A | 5/1966 | Blume | |
| 3,657,571 A | 4/1972 | Martin et al. | |
| 3,693,403 A | 9/1972 | Paul | |
| 4,541,269 A | 9/1985 | Thomas | |
| 5,116,764 A | 5/1992 | Annino et al. | |
| 5,611,846 A | 3/1997 | Overton et al. | |
| 5,958,246 A | 9/1999 | Tipler et al. | |
| 5,979,221 A | 11/1999 | Walte et al. | |
| 6,040,191 A * | 3/2000 | Grow ..................... 506/12 |
| 6,156,196 A * | 12/2000 | Gao ..................... 210/198.2 |
| 6,251,344 B1 | 6/2001 | Goldstein | |

(Continued)

FOREIGN PATENT DOCUMENTS

WO     WO 2005/057177     6/2005

(Continued)

OTHER PUBLICATIONS

Wordsmyth web page showing definition of "data processing" (no date).

(Continued)

*Primary Examiner*—Carol S Tsai
*Assistant Examiner*—Felix E Suarez
(74) *Attorney, Agent, or Firm*—Thorpe North & Western LLP

(57) ABSTRACT

An apparatus, system, and method are disclosed for broad spectrum chemical detection. The method includes determining a similarity sequencing scheme. The method includes receiving an ambient air sample and concentrating the ambient air sample. The method further includes providing the concentrated sample to a gas chromatography (GC) column, and detecting chemical elution from the GC column in a series of similarity sequenced samples based on the similarity sequencing scheme. The method includes de-convoluting the elution data to derive arrival peaks, and determining a concentration of a chemical in the ambient air based on the series of constant log-time data samples. In one embodiment, the method utilizes a modified Z-transform to de-convolute the elution data.

23 Claims, 27 Drawing Sheets

U.S. PATENT DOCUMENTS

| | | |
|---|---|---|
| 6,506,384 B1 * | 1/2003 | Laal et al. ............... 424/168.1 |
| 6,579,345 B2 | 6/2003 | Munari et al. |
| 6,680,203 B2 * | 1/2004 | Dasseux et al. ............... 436/86 |
| 6,797,242 B2 | 9/2004 | Nuemann et al. |
| 6,816,789 B2 | 11/2004 | Excoffier |
| 6,837,096 B2 | 1/2005 | Stewart |
| 2002/0016524 A1 | 2/2002 | Messier et al. |
| 2002/0148353 A1 | 10/2002 | Seeley |
| 2004/0005240 A1 | 1/2004 | Adiga et al. |
| 2004/0019428 A1 | 1/2004 | Young et al. |
| 2004/0022679 A1 | 2/2004 | St. Onge et al. |
| 2004/0120845 A1 | 6/2004 | Potember et al. |
| 2005/0008529 A1 | 1/2005 | Nuemann et al. |
| 2005/0175500 A1 | 8/2005 | Adams et al. |
| 2005/0269254 A1 | 12/2005 | Roitman |
| 2006/0008379 A1 | 1/2006 | Mielnik et al. |
| 2006/0051782 A1 * | 3/2006 | Wood et al. ............... 435/6 |
| 2006/0140817 A1 | 6/2006 | Cumberland et al. |
| 2007/0029477 A1 | 2/2007 | Miller et al. |
| 2008/0016943 A1 | 1/2008 | Arnold et al. |
| 2008/0105119 A1 | 5/2008 | Arnold et al. |

OTHER PUBLICATIONS

Merriam-Webster online dictionary web page showing definition of "data processing" (no date).

* cited by examiner

APPARATUS, SYSTEM, AND METHOD FOR BROAD SPECTRUM CHEMICAL DETECTION

CROSS-REFERENCES TO RELATED APPLICATIONS

This application claims benefit of U.S. Patent Application No. 60/805,309 entitled "APPARATUS, SYSTEM, AND METHOD FOR BROAD SPECTRUM CHEMICAL DETECTION" and filed on Jun. 20, 2006 for Arnold et al., which is incorporated herein by reference.

BACKGROUND OF THE INVENTION

1. Field of the Invention

This invention relates to chemical detectors and more particularly relates to gas chromatography sensors.

2. Description of the Related Art

Gas chromatography (GC) is useful in the chemical industry as a separation mechanism and as a sensing mechanism. GC sensors are extremely useful for detecting specific chemicals in a gas with mixed components, but they suffer from the major drawback that they are quite expensive.

The required purities in GC mandate, within most of the current art, the use of valves that cost in the thousands of dollars per valve. One concept has been introduced which allows air pressure to perform some of the gas switching, which allows the expensive valves to be replaced with cheaper solenoid valves, see U.S. Pat. No. 4,970,905. However, the present art for accomplishing this requires complicated machining and assembly causing manufacturing expense and reliability problems.

Another limitation of the present art is that manufacture of GC columns is a tedious and expensive process. For example, the GC column must be heated uniformly while in use, and low cost methods to effectively accomplish this uniform heating are lacking in the present art. One current method to provide effective and affordable heating is to co-axially winding a heating element around the GC column—this method is expensive to implement. There are temperature control methods which are easy to manufacture, but which tend to leave the GC column directly exposed to a heating element and thus allow for non-uniform temperature spikes at places along the GC column.

Another limitation of current GC sensor technology is that the sensors need to be periodically calibrated against an internal standard, and no cheap methods exist to provide for this. The current technology is to provide a chemical, which must be stored, and an injection mechanism which must inject the chemical into the system without interfering with seals and the normal operation of the GC sensor.

GC sensors typically use a preconcentration mechanism, which multiplies the concentration of chemicals of interest in a sample and allows detection of lower initial concentrations than otherwise allowable. Typically, an absorption-desorption material is added into the sample stream to accomplish this. Current methods of adding adsorption-desorption materials tend to cause variable pressure drop in the sensor flow paths.

In the current art, the GC sensor must operate at a design operational temperature. Lower temperatures are desirable for better separation of elution times of different components, while higher temperatures improve the sensor response time. However, the test temperature must be at least as high as the ambient temperature. Typically, an operating temperature is selected that is higher than any predicted ambient temperature when the GC sensor is manufactured. This causes the temperature to be set higher than necessary when the actual ambient temperature is low, making chemical detection more difficult than required, and inducing greater energy loss to heat the GC sensor than would otherwise be required.

In GC sensors that detect a wide range of chemicals, the chemicals can have widely variable elution times from the GC column. Further, the shape of the detection peaks for chemicals with different elution times will vary. As a general principle, later eluting chemicals will have a lower and wider peak than early eluting chemicals. Further, in high resolution GC sensors that are detecting concentrations in the parts-per-million (ppm) and parts-per-billion (ppb) ranges, extraneous peaks and noise will occur in the basic signal. This variability in peak shape makes it difficult for detection algorithms to correlate the concentrations of the various chemicals.

A GC sensor will typically have a long GC column placed into a small area, and will typically be wound up as tight as possible. Further, the GC column may be manufactured in one time and location, and transported and/or stored for a period before assembly of the GC sensor. A cheap method to build uniform GC columns, and to protect the columns from the introduction of impurities between the time of manufacture and the time of assembly is desirable.

A dual hyphenated GC sensor, and any GC sensor that is either utilized to detect many chemicals simultaneously, or utilized to detect chemicals from a complex mixture of gases, suffers in the current art from difficulty in finding chemical elution peaks within a complex signal. Often a significant amount of noise is produced in the signal. The standard Fourier analysis of GC signals suffer from producing ringing in the signal, especially with high frequency components of the signal. Noise suppression wavelets are known in the art, but any particular noise suppression wavelet will still tend to leave some noise peaks in the signal and complex signals continue to be difficult to interpret.

Proper sealing of GC sensors is a known difficulty in the art, and is especially problematic in sensors attempting to detect chemicals at the low parts-per-million (ppm), or even into the parts-per-billion (ppb) range. The internal flowpaths of the sensor must be protected from leakage to the ambient environment, and the analytical flowpaths containing the chemical sample must be further protected from undesigned fluid migration within the sensor.

From the foregoing discussion, it should be apparent that a need exists for an apparatus, system, and method that detects a broad spectrum of chemicals in a GC sensor in an inexpensive and effective manner. Beneficially, such an apparatus, system, and method would allow the use of inexpensive solenoid valves, provide for easy manufacture, provide for uniform and inexpensive heating of sensing elements, allow for a low cost implementation of an internal chemical standard, provide for manufacture of a preconcentration system that is inexpensive and provides uniform pressure drop, allows low energy operation in a wide range of ambient environments, that robustly detects chemicals that have widely varying elution times, and that is protected from leakage from the ambient environment and internally within the analytical flowpaths.

SUMMARY OF THE INVENTION

Based on the foregoing, the Applicant asserts that a need exists for a system, method, and apparatus for broad spectrum chemical detection. Beneficially, the system, method, and apparatus would allow detection of chemicals with widely varying elution times in a GC sensor, including allowing the use of a simple de-convolution transform even where elution times vary significantly. The present invention has been developed in response to the present state of the art, and in particular, in response to the problems and needs in the art that have not yet been fully solved by currently available GC sensor technology. Accordingly, the present invention has been developed to provide an apparatus, system, and method for broad spectrum chemical detection that overcome many or all of the above-discussed shortcomings in the art.

A system for detecting chemicals with a gas chromatography sensor is disclosed. The system includes a gas chromatography (GC) sensor comprising dual GC columns, and a controller. The controller includes modules configured to functionally execute the operations of detecting chemicals in the GC sensor. In one embodiment, the modules include a similarity definition module, an elution data module, a similarity sequencing module, a chemical detection module, a signal processing module, and a noise filtering module. The similarity definition module determines a similarity sequencing scheme. The elution data module interprets elution data signals from at least one gas chromatography (GC) column. The similarity sequencing module sorts the elution data signals into a series of similarity sequenced samples based on the similarity sequencing scheme. The chemical detection module determines a concentration of at least one chemical in the ambient air sample based on the series of similarity sequenced samples. The signal processing module de-convolutes the series of similarity sequenced samples to determine a plurality of arrival peaks. The noise-filtering module operates at least one noise wavelet on the plurality of arrival peaks to determine whether each arrival peak comprises one of noise and data.

A method for detecting chemicals with a gas chromatography sensor is disclosed. The method includes determining a similarity sequencing scheme. The method further includes receiving an ambient air sample and concentrating the ambient air sample. The method further includes providing the concentrated sample to at least one GC column and detecting chemical elution from the at least one GC column in a series of similarity sequenced samples according to the similarity sequencing scheme. The method further includes determining a concentration of at least one chemical in the ambient air sample based on the series of similarity sequenced samples.

In one embodiment, detecting chemical elution from the at least one GC column in a series of similarity sequenced samples includes sampling elution data from the at least one GC column in time steps defined by the similarity sequencing scheme. In an alternate embodiment, the method includes detecting chemical elution from the at least one GC column in a series of similarity sequenced samples by sampling elution data from the at least one GC column in constant-time increments, and transforming the constant-time increment data to time step data defined by the similarity sequencing scheme.

The method includes determining a concentration of at least one chemical in the ambient air sample based on the series of similarity sequenced samples by deriving elution data from the series of similarity sequenced samples, and de-convoluting the elution data to derive a plurality of arrival peaks. In one embodiment, the method includes checking the plurality of arrival peaks against a database of chemical signatures. The method further includes determining the concentration of the at least one chemical in the ambient air sample based on an arrival time and integrated area of one of the plurality of arrival peaks. The method further includes determining the integrated area of one of the plurality of arrival peaks according to a rectangular approximation.

In one embodiment, the method includes de-convoluting the elution data utilizing a Z-transform to de-convolute the elution data. Utilizing the Z-transform may include applying a Z-transform on the elution data in sample space, wherein the Z-transform of an input data set is estimated to be the Z-transform of the elution data divided by a Z-transform of an estimated system. The Z-transform of the estimated system is assumed to be constant for each of the plurality of arrival peaks.

The method may further include operating at least one noise wavelet on the plurality of arrival peaks to determine whether each arrival peak comprises one of noise and data. In one embodiment, the method includes determining a peak to be relatively stable in response to the peak reappearing after operating the at least one noise wavelet within a specified range of amplitude and time values, and determining a peak to be data in response to determining the peak to be relatively stable. In one embodiment, the method further includes operating a set of noise wavelets on the plurality of arrival peaks to determine whether each arrival peak comprises one of noise and data. The method may further include operating a random subset of noise wavelets from a set of noise wavelets on the plurality of arrival peaks to determine whether each arrival peak comprises one of noise and data. The method further includes operating at least one primary noise wavelet on the plurality of arrival peaks, and operating a random subset of secondary noise wavelets from a set of secondary noise wavelets on the plurality of arrival peaks, to determine whether each arrival peak comprises one of noise and data, in one embodiment.

An apparatus is disclosed for detecting chemicals with a GC sensor. The apparatus includes a plurality of modules configured to functionally execute the operations of detecting chemicals. In one embodiment, the apparatus includes an elution data module, a similarity sequencing module, and a chemical detection module. The apparatus may further include a signal processing module and a noise-filtering module.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1A:
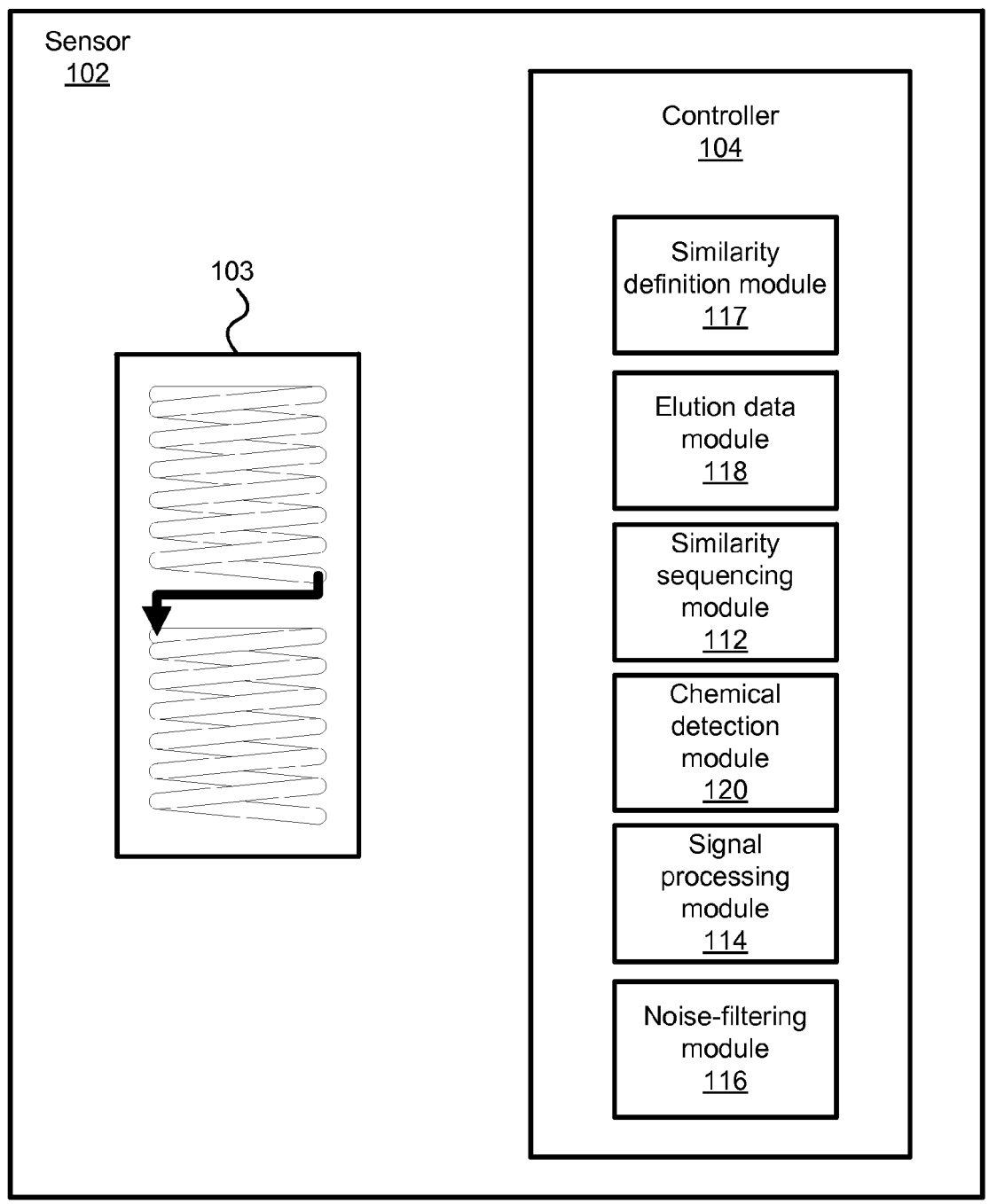
FIG. 1A is a schematic block diagram illustrating one embodiment of a system to detect a broad spectrum of chemicals in accordance with the present invention.

It will be readily understood that the components of the present invention, as generally described and illustrated in the figures herein, may be arranged and designed in a wide variety of different configurations. Thus, the following more detailed description of the embodiments of the apparatus, system, and method of the present invention, as presented in FIGS. 1 through 23, is not intended to limit the scope of the invention, as claimed, but is merely representative of selected embodiments of the invention.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided, such as examples of materials, fasteners, sizes, lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

FIG. 1A is a schematic block diagram illustrating one embodiment of a system 101 to detect a broad spectrum of chemicals in accordance with the present invention. The system 101 includes a gas chromatography (GC) sensor 102 comprising dual GC columns 103, and a controller 104. The controller 104 includes modules configured to functionally execute the operations of detecting chemicals in the GC sensor 102. In one embodiment, the modules include a similarity definition module 117, an elution data module 118, a similarity sequencing module 112, a chemical detection module 120, a signal processing module 114, and a noise filtering module 116. The similarity definition module 117 determines a similarity sequencing scheme. The elution data module 118 interprets elution data signals from at least one gas chromatography (GC) column. The similarity sequencing module 112 sorts the elution data signals into a series of similarity sequenced samples based on the similarity sequencing scheme. The signal processing module 114 de-convolutes the series of similarity sequenced samples to determine a plurality of arrival peaks. The noise-filtering module 116 operates at least one noise wavelet on the plurality of arrival peaks to determine whether each arrival peak comprises one of noise and data.

The chemical detection module 120 determines a concentration of at least one chemical in the ambient air sample based on the series of similarity sequenced samples. In one embodiment, the chemical detection module 120 determines the concentration of at least one chemical in the ambient air sample based on the series of similarity sequenced samples by checking a peak time occurrence and a peak integrated area based on the de-convoluted and noise filtered peaks after processing by the signal processing module 114 and noise-filtering module 116. The time of occurrence of a peak may indicate the chemical present, and the integrated area of the peak may indicate the amount of the chemical present, which is equated to the concentration.

Figure 1B:
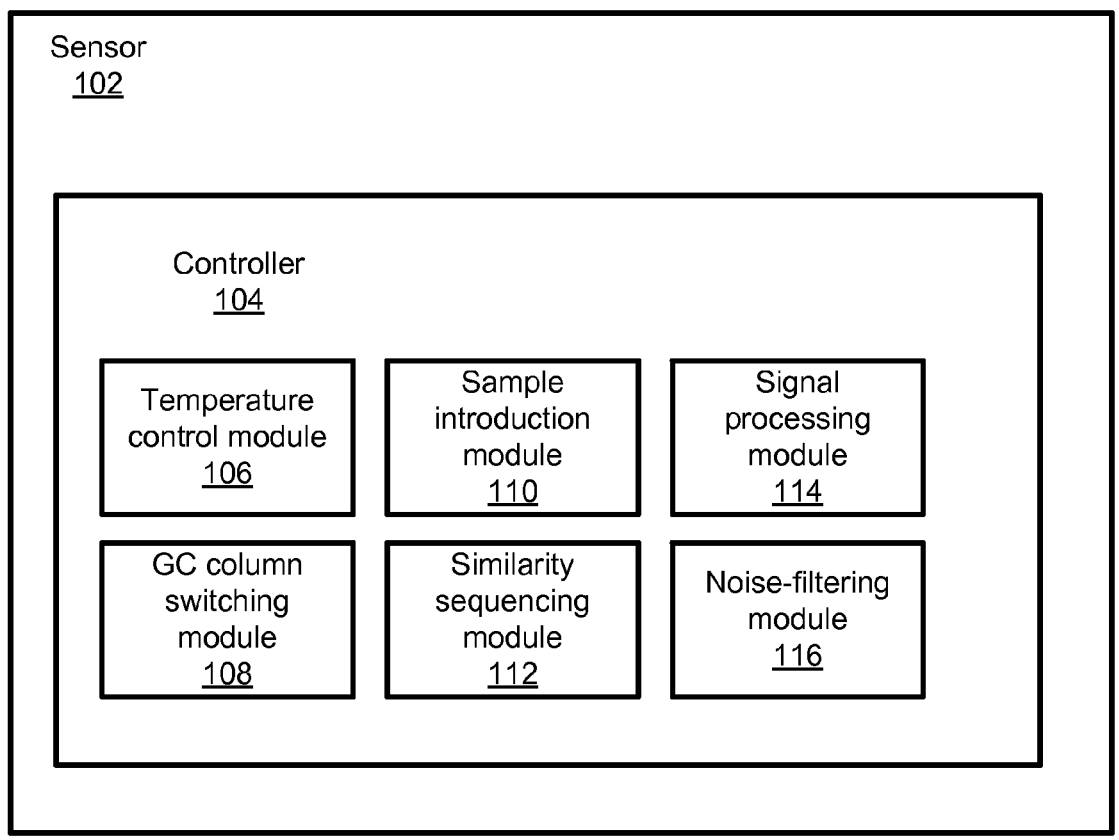
FIG. 1B is a schematic block diagram illustrating an alternate embodiment of a system to detect a broad spectrum of chemicals in accordance with the present invention.

FIG. 1B is a schematic block diagram illustrating one embodiment of a system 100 to detect a broad spectrum of chemicals in accordance with the present invention. The system 100 may comprise a gas chromatography (GC) sensor, and a controller 104. The controller may comprise at least one module configured to control one or more aspects of the GC sensor. The modules in one embodiment may comprise a temperature control module 106, a GC column switching module 108, a sample introduction module 110, a similarity sequencing module 112, a signal processing module 114, and a noise-filtering module 116.

The temperature control module 106 may be configured to control the temperature of one or more GC columns within the GC sensor. The temperature control module may be configured to control the temperature of the GC column(s) based on the current ambient temperature and a set of chemical elution data corresponding to a set of temperatures.

The GC column switching module 108 may be configured to control gas flows through at least one GC column in the GC sensor 102. The GC column switching module 108 may be configured to control the flows such that a gas flow passes through a first GC column into a second GC column in series. The GC column switching module 108 may be further configured to control the flows such that a first and second GC column each receive a gas flow in parallel. The GC column switching module 108 may be further configured to ensure that a first and second GC column receive substantially the same flow rate of gas.

The sample introduction module 110 maybe configured to introduce a sample gas into at least one GC column. The sample introduction module 110 may be configured to control a sample flow in a concentration flow regime configured to concentrate a sample gas onto a preconcentration material, which may be configured to adsorb the sampled chemicals of interest. The sample introduction module 110 may be further configured to control a sample flow in a desorption flow regime to desorb a sample gas from the preconcentration material, and to flow the concentrated sample through the at least one GC column.

The similarity sequencing module 112 may be configured to take data samples in a constant log-time fashion to ensure that early eluting and late eluting chemicals exhibit qualitatively similar data peaks. The similarity sequencing module 112 may be configured in one embodiment to take data samples in a constant time fashion, and to process the data to simulate a constant log-time data set.

The signal processing module 114 may be configured to deconvolute a sampling data set to determine the chemical inputs to the at least one GC column that generate the eluted chemicals observed in the sampling data. The signal processing module 114 may be configured to deconvolute the sampling data utilizing a Z-transform. The signal processing module 114 may be configured to convert the sequential sampling data into a high order polynomial, divide the high order polynomial by a polynomial system model, and thereby generate a an input polynomial. The signal processing module 114 may be further configured to regenerate the predicted input signal by an inverse Z-transform of the input polynomial. The Z-transform may be modified to use the largest polynomial divisor possible without generating negative values. The modified Z-transform may be enabled by the near-constant width in sample space of the chemical elution peaks generated by the similarity sequencing module 112.

The noise filtering module 116 may be configured to operate a noise suppression wavelet and/or other noise suppression method on the sampling data to suppress noise peaks. The noise filtering module 116 may be further configured to operate a plurality of noise suppression wavelets on the sampling data, and to identify one or more peaks as noise, and one or more peaks as data. The noise filtering module 116 may be configured to identify relatively stable peaks as data, and relatively unstable peaks as noise.

Figure 2A:
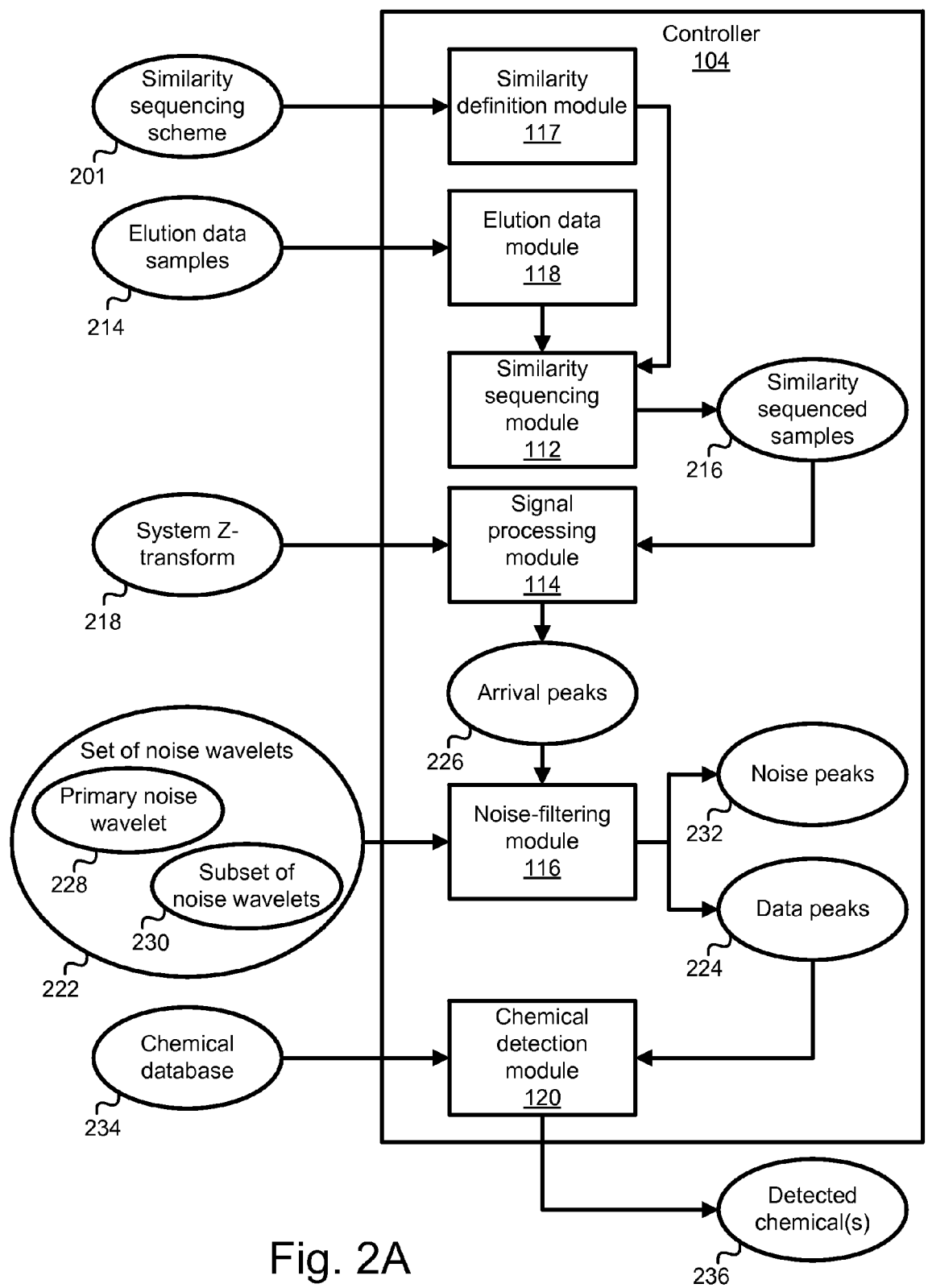
FIG. 2A is a schematic block diagram illustrating one embodiment of a controller for a GC sensor in accordance with the present invention.

FIG. 2A is a schematic block diagram illustrating one embodiment of a controller 104 for a GC sensor 102 in accordance with the present invention. The controller 104 includes a similarity definition module 117 that determines a similarity sequencing scheme 201. In one embodiment, a similarity sequencing scheme 201 is a time sampling profile wherein, if elution data samples 214 are taken for slow-eluting chemicals and for fast-eluting chemicals in the GC sensor 102, both slow-eluting chemicals and fast-eluting chemicals will exhibit similar elution peak characteristics as measured by the width and number of samples defining the elution peak.

The controller 104 includes an elution data module 118 that interprets elution data signals (samples) 214 from at least one GC column. The controller 104 further includes a similarity sequencing module 112 that sorts the elution data signals 214 into a series of similarity sequenced samples 216.

In one embodiment, the controller 104 includes a signal processing module 114 that de-convolutes the similarity sequenced samples 216 utilizing a modified Z-transform to determine a plurality of arrival peaks 226. In one embodiment, the signal processing module 114 de-convolutes the similarity sequenced samples 216 by dividing the Z-transform of the output (the measured similarity sequenced samples 216) by the Z-transform of the system 218 to determine the Z-transform of the input and thereby the chemical concentrations introduced into the GC columns. The use of similarity sequenced samples 216 makes fast-eluting chemicals and slow-eluting chemicals exhibit similar peak behaviors (e.g. the width of the peaks in the X axis, time domain, or modified-time domain) and thereby makes the system Z-transform 218 appear to be similar for all chemicals of interest. The use of the same or similar system Z-transform 218 for all chemicals is a modified Z-transform as used herein. The Z-transform of the system 218 describes the dynamics (mass diffusion, etc.) of the GC columns, in one embodiment.

The de-convoluted data yields a plurality of arrival peaks 226 describing chemicals introduced to the GC columns. However, some of the arrival peaks 226 may comprise noise rather than data. The controller 104 may include a noise-filtering module 116 that applies one or more noise wavelets 222 to the arrival peaks 226 to determine whether each arrival peak 226 comprises one of a noise peak 232 or a data peak 224. In one embodiment, the noise-filtering module 116 applies a single noise wavelet, and checks for stable peaks. Stable peaks may be considered to be data 224, while unstable peaks may be considered to be noise 232. Stability may include an amplitude threshold and a time threshold, wherein if a peak 226 reappears within the amplitude threshold and/or the time threshold of the pre-noise wavelet 222 application values, the peak 226 is considered stable.

In one embodiment, the noise-filtering module 116 applies a set of noise wavelets 222 to the arrival peaks 226. In an alternate embodiment, the noise-filtering module 116 applies a random subset 230 of the set of noise wavelets 222 to the arrival peaks 226. In an alternate embodiment, the noise-filtering module 116 applies a primary noise wavelet 228 to the arrival peaks 226, and a random subset of the subset of noise wavelets 230 to the arrival peaks 226.

The controller 104 includes a chemical detection module 120 that determines a concentration of at least one chemical in the ambient air sample based on the series of similarity sequenced samples 216. In one embodiment, the chemical detection module 120 determines the concentration of the at least one chemical in the ambient air sample based on the series of similarity sequenced samples 216 by checking the data peaks 224 against a chemical database 234 to determine whether the data peaks 224 indicate the presence of any chemicals of interest. The detected chemicals 236 may be reported as a data element stored and/or communicated in an electronic medium, a sensor 102 physical response, and the like.

Figure 2B:
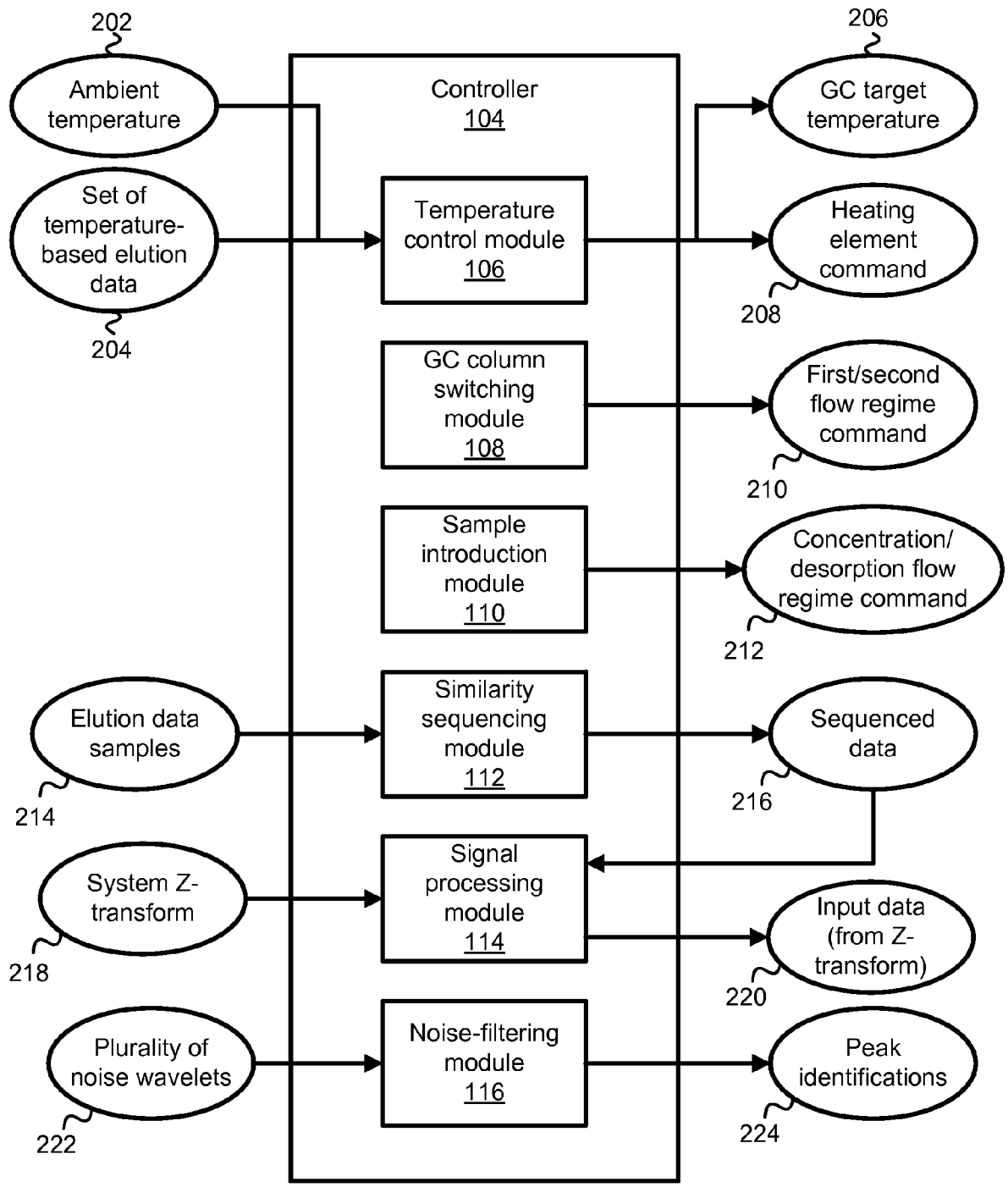
FIG. 2B is a schematic block diagram illustrating an alternate embodiment of a controller for a GC sensor in accordance with the present invention.

FIG. 2B is a schematic block diagram illustrating one embodiment of a controller 104 for a GC sensor 102 in accordance with the present invention. The controller 104 may comprise a plurality of modules to functionally execute the controller 104 operations.

The controller 104 may comprise a temperature control module 106 configured to maintain a GC target temperature 206 at a lowest feasible temperature to maintain elution time separation of closely related chemicals and to minimize the heating burden on the GC sensor 102. The temperature control module 106 may be configured to determine an ambient temperature 202. The temperature control module 106 may be further configured to read a stored set of temperature-based elution data 204. The temperature control module 106 may then select a GC target temperature 206 based on the ambient temperature 202 and the set of temperature-based elution data 204.

In one embodiment, the temperature control module 106 may be configured to select the next available temperature from the set of temperature-based elution data 204 higher than the ambient temperature 202. In one example, the set of temperature-based elution data 204 comprises elution data 204 at 50° F., 100° F., and 150° F. In the example, the temperature control module 106 may select a GC target temperature of 100° F. when the ambient temperature 202 is 65° F.

In one embodiment, the temperature control module 106 maybe configured to interpolate elution data between available temperatures in the set of temperature-based elution data 204, and may be configured to select a GC target temperature 206 at any desired temperature. For example, the set of temperature-based elution data 204 may comprise elution data 204 at 50° F., 100° F., and 150° F., and the temperature-based elution data 204 may be configured to select a GC target temperature 10° F. higher than the ambient temperature 202, or 75° F. when the ambient temperature 202 is 65° F. The interpolation may be simple interpolation, or where greater accuracy is required the interpolation could occur through the application of fundamental mass diffusion equations.

The temperature control module 106 may be further configured to provide a heating element command 208, which may be a physical control of a heating element, a datalink command to another portion of the controller 104 to control the heating element, or the like. The heating element may be controlled through a standard control scheme such as a proportional-integral-derivative (PID) controller to control the GC column(s) to the GC target temperature 206.

In one embodiment, the set of temperature-based elution data 204 contains one set of data for a first GC column, and a second set of data for a second GC column. The GC target temperature 206 may comprise a target temperature 206 for each GC column, and the target temperatures 206 may be different values for each GC column.

The controller 104 may comprise a GC column switching module 108 configured to control gas flows through at least one GC column in the GC sensor 102. The GC column switching module 108 may be configured to control the flows in a first flow regime 210 such that a gas flow passes through a first GC column into a second GC column in series. The GC column switching module 108 may be further configured to control the flows in a second flow regime 210 such that a first and second GC column each receive a gas flow in parallel. The GC column switching module 108 may be further configured to ensure that a first and second GC column receive substantially the same flow rate of gas.

The GC column switching module 108 may comprise commands to one or more valves and one or more pumps to achieve the flow regime switches. The commands may comprise physical control of the valves and/or pumps, a datalink command to another portion of the controller 104, or the like.

The controller 104 may comprise a sample introduction module 110 configured to introduce a sample gas into at least one GC column. The sample introduction module 110 may be configured to control a sample flow in a concentration flow regime 212 configured to concentrate a sample gas onto a preconcentration material, which may be configured to adsorb the sampled chemicals of interest. The sample introduction module 110 may be further configured to control a sample flow in a desorption flow regime 212 to desorb a sample gas from the preconcentration material, and to flow the concentrated sample through the at least one GC column.

The sample introduction module 108 may comprise commands to one or more valves and one or more pumps to achieve the flow regime switches. The commands may comprise physical control of the valves and/or pumps, a datalink command to another portion of the controller 104, or the like.

The controller 104 may comprise a similarity sequencing module 112 configured to take data samples in a constant log-time fashion. Early eluting chemicals tend to have a sharper peak shape and to elute in a short period of time. Later eluting chemicals tend to have a flatter peak shape and to elute over a longer period of time. Therefore, the later eluting chemicals tend to have a peak created from a much larger number of samples than earlier eluting peaks, and the different shapes of the peaks tend to make algorithms less likely to detect them. Taking data in a constant log-time fashion tends to clean up the peaks and make early and late eluting chemicals show similar looking peaks. In one example, the similarity sequencing module 112 may be configured to take data samples 214 at each 0.2 log seconds, or the normal time value of data point value "n" equals $e\hat{\ }n$. In the example, data point 12 would be (12*0.2=) log-time 2.4, and the normal time value would be 11.02 seconds. Logarithm values other than base "e", or the natural logarithm, are possible, as the natural logarithm is used only for illustration.

Many applications have a natural data sampling frequency due to controller 104 execution times and physical limitations of the sensor 102. Therefore, the similarity sequencing module 112 may be configured in one embodiment to take data samples 214 in a constant time fashion, and to process the data to simulate a constant log-time data set 216. For example, the similarity sequencing module may be configured to physically collect data each 0.2 seconds. To simulate the $15^{th}$ log-time data point, the time data from ($e\hat{\ }(15*0.2)=$) 20.08 seconds to ($e\hat{\ }(16*0.2)=$) 24.53 seconds would be used. Therefore, the constant time data points (214) 101-122, as well as part of data point 100, and part of data point 123, would be integrated to simulate the $15^{th}$ log-time data point 216.

A rectangular approximation or other integrating algorithm could be used to integrate the data between the given sample points 214. Simpson's rule, trapezoidal, and polynomial approximations can be used as well, although those integrating algorithms provide little benefit of improved accuracy over a rectangular approximation where the constant time data interval is small, and those algorithms, for example Simpson's rule, may amplify high frequency signal noise.

The signal processing module 114 may be configured to deconvolute a sampling data set 216 to clarify data peaks and find eluted chemicals in the sampling data. The sampled data set 216 may be affected in time, or convoluted, due to diffusion and separation in the at least one GC tube. The deconvolution process may recover the original signal, which is typically a chemical concentration in GC sensors 102. The signal processing module 114 may be configured to deconvolute the data set 216 with the largest polynomial division that does not produce an unstable data response. The signal processing module 114 may be further configured to utilize a Z-transform in sampling point space to determine the input signal according to the following equation where the Z-transform of the system 218 may be a transfer function describing the characteristics of the system:

$$\frac{Z(output)}{Z(system)} = Z(input). \quad \text{Equation 1}$$

Therefore, the inverse transform of the result of Equation 1 provides the input data 220 or the information from the sampling data input. A Fourier transform can also be used in deriving the data, although the Fourier transform is more susceptible to ringing from high frequency noise.

The signal processing module 114 may be configured to deconvolute the sampling data set to clarify data peaks and find eluted chemicals in the sampling data by converting the sampling data set 216 into a high order polynomial, for example by a regression fit. The signal processing module 114 may be further configured to interpret a model 218 of the GC column system, which may be a transform function in the form $N_Z/D_Z$, or a rational polynomial function. In some embodiments, either $N_Z$ or $D_Z$ may be 1, reducing the transform function to $1/D_Z$ or $N_Z$, respectively. Those of skill in the art will recognize that if the roots of $D_Z$ fall within the unit circle, the signal convolution is stable.

The signal processing module 114 may be configured to label the input chemical sample function as U, the output function as Y, and the system model as G, and to label the Z-transforms of those functions as $U_Z$, $Y_Z$, and $G_Z$. The input function may be convoluted by the GC columns such that $Y_Z = G_Z * U_Z$, where $Y_Z$ is the measured output at the detector, and $U_Z$ is the Z-transformed desired input information. Therefore, it is apparent that equation 2 yields the desired input information.

$$Z^{-1}(Uz) = Z^{-1}(Yz/Gz) = Z^{-1}((Yz*Dz)/Nz) \quad \text{Equation 2.}$$

The signal processing module 114 may be configured to modify the Z-transform division to ensure it is stable. This may be accomplished with a standard division configured to avoid a negative result. In the following example, polynomials are expressed as coefficients only without the related powers (e.g. $X^2 + 2X + 3 = [1\ 2\ 3]$). In one example, $N_Z$ may be [3 2 1 2 3 2 1] while $D_Z$ may be [1 1 1]. The first factor to check may be 3/1=3, generating a first intermediate result of (3 −3*1 2 −3*1 1 −3*1 2 3 2 1), or (0 −1 −2 2 3 2 1) with the result being (1). Note that the result contains negative values, and is therefore unstable. The second intermediate result is (0 0 −4 0 3 2 1) with the result being (1 −1). The next becomes (0 0 0 −4 −1 2 1) result =(1 −1 −4). The result begins to show wild fluctuations in the example.

Continuing the analysis by testing factors under the restriction of no negative results, it is apparent that the first factor for the example should be 1. With 1 the result will be (2 1 0 2 3 2 1). As there are no negative values this is acceptable. Proceeding to the next factor, 1 is first selected. Selecting 1 also produces negative values so it is reduced to 0. The second result would be (2 1 0 2 3 2 1) with the result being (1 0). The third is (2 1 0 2 3 2 1) with the result (1 0 0), the fourth is (2 1 0 0 1 0 1) and (1 0 0 2). Continuing to the end yields (2 1 0 0 1 0 1)and(1 0 0 2 0 0 0).

The signal processing module 114 may be configured to complete the deconvolution under equation 2. The modified Z-transform takes care of any instability introduced by any problematic zeros. Note that the modified z transform method makes an implicit assumption that all features of interest convolute similarly as the divisor is constant. If the divisor is not constant, for example because the width of peaks of interest increases at later elute times then further modification may be utilized. A first modification is to change the divisor for each time period of interest. This is within the skill of one in the art, but may not be the preferable solution in some circumstances. A second modification is to adjust the time sampling such that the peaks have similar features and the constant divisor remains valid. The similarity sequencing module 112 may be configured to perform the second modification, wherein the use of constant log-time data samples creates peaks with similar features and validates the constant divisor. In embodiments utilizing a Fourier transform or other deconvolution methods, the divisor issue remains and therefore the constant log-time data samples may still be utilized in those embodiments.

The noise filtering module 116 may be configured to operate a plurality of noise suppression wavelets 222 and/or other noise suppression methods on the sampling data, and to identify one or more peaks as noise, and one or more peaks as data. Each noise suppression methodology may make assumptions about the noise shape. These assumptions are known as the noise model. Changing the noise model will affect the result of the noise suppression step, which will introduce or eliminate different noise generated artifacts in the results.

The noise filtering module 116 may be further configured to identify relatively stable peaks as data, and relatively unstable peaks as noise. A stable peak in this context is a peak that is present even when several noise suppression methods are used. An unstable peak is one whose presence is dependent on the noise model used and thus is not present in some of the responses. The noise filtering module 116 may be configured to operate a noise suppression wavelet 222 or other noise suppression method on the sampling data to suppress noise peaks. The noise filtering module 116 may be further configured to operate a plurality of noise suppression wavelets 222 on the sampling data, and to identify one or more peaks as noise 224, and one or more peaks as data 224. The noise filtering module 116 may be configured to identify relatively stable peaks as data, and relatively unstable peaks as noise In one embodiment, the noise filtering module 116 may be configured to operate a set number of noise filtering wavelets 222 on the sampling data at each time step, and to identify peaks 224 which remain substantially constant as data, and peaks 224 which move or intermittently appear as noise. Substantially constant may comprise a range of amplitudes and a range of time values wherein a peak can appear and still be considered to be the same peak. Moving or intermittently appearing may comprise values outside of the range of amplitudes and the range of time values wherein a peak can appear and still be considered to be the same peak.

In one embodiment, the noise filtering module 116 may be configured with a larger number of noise suppression wavelets 222 than the noise filtering module 116 may run on each execution time step. In one example, the noise filtering module 116 may comprise ten noise suppression wavelets 222, and the noise filtering module 116 may operate three noise suppression wavelets 222 at each time step. The three noise suppression wavelets may comprise a random selection from the ten available wavelets 222, a rotation within the ten available wavelets 222, or a primary noise suppression wavelet 222 and two wavelets selected from the other nine available wavelets 222. This embodiment avoids having a noise suppression wavelet 222 that may be sensitive in some operating conditions dominate the signal, while improving the operational performance of the controller 104 compared to running all wavelets 222 at every execution cycle.

Figure 3:
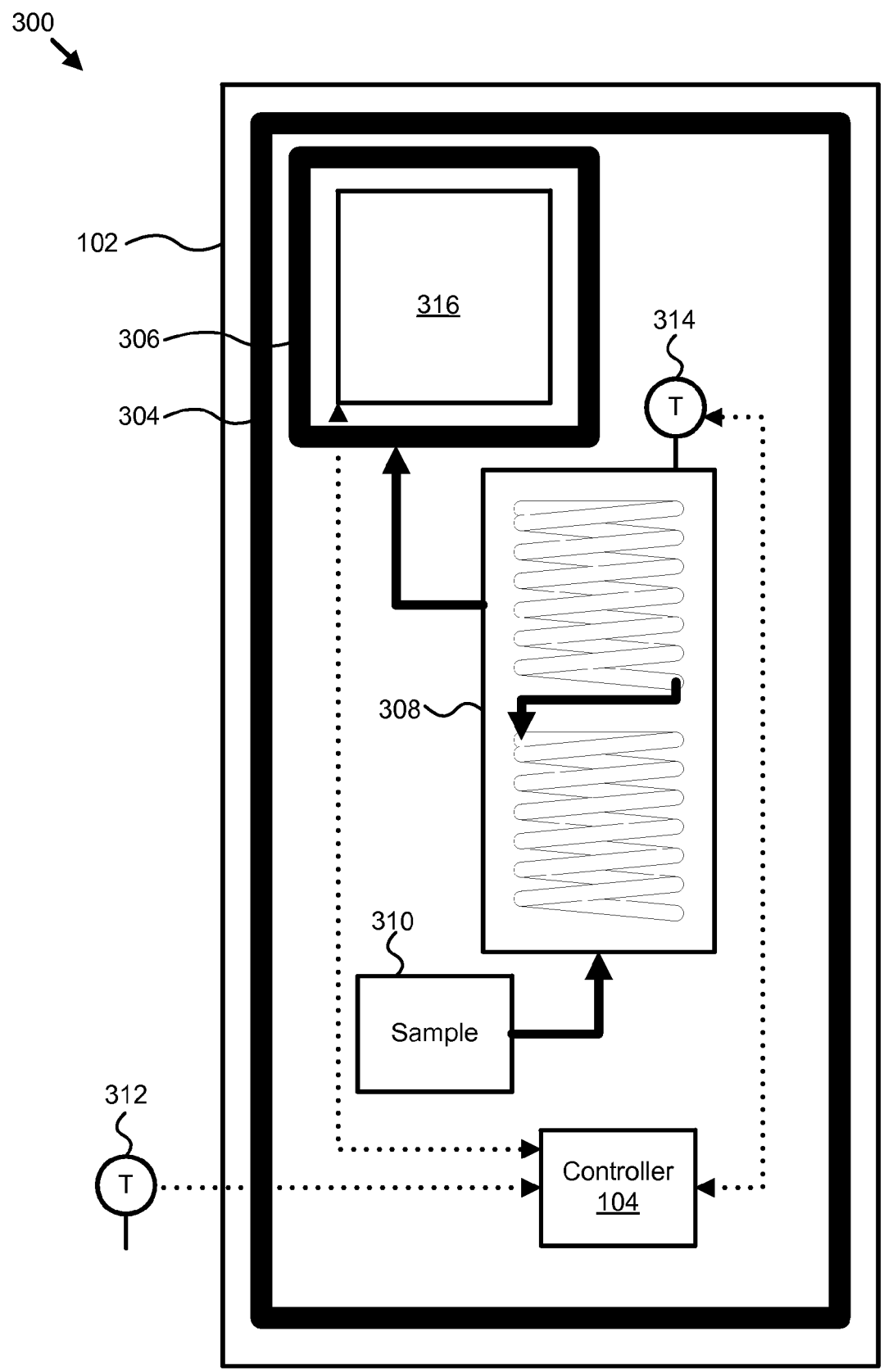
FIG. 3 is a schematic block diagram illustrating one embodiment of an apparatus to seal a GC sensor and detector circuit in accordance with the present invention.

FIG. 3 is a schematic block diagram illustrating one embodiment of an apparatus 300 to seal a GC sensor 102 and detector circuit 316 in accordance with the present invention. The apparatus 300 may comprise a first sealing surface 304 configured to seal the sensor 102 from an ambient environment. The first sealing surface 304 may be an epoxy or similar sealant configured to seal the material of the sensor 102 body which may comprise a machineable ceramic. In one embodiment, an acrylic GP sealant is used at the sealing surface 304. The apparatus 300 may further comprise a second sealing surface 306 configured to seal a detector circuit 316 from internal leaks within the sensor 102.

The apparatus may further comprise a GC unit 308 which may comprise at least one GC column, and a sample unit 310 configured to provide the sample gas to the sensor 102 and GC unit 308. The sample may pass from the GC unit 308 to the detector 316. The detector 316 may comprise any detection device used in the GC art—including a thermal conductivity detector (TCD), a mass spectrometer, flame ionization detector, photo-ionization detector, electron capture detector, Hall electrolytic conductivity detector, and the like. In one embodiment, the detector 316 comprises a TCD, and the detector 316 is configured to generate an electrical signal based on the detected thermal conductivity of the sample gas on one side of a Wheatstone bridge, with an electrical signal based on the detected thermal conductivity of a reference gas on the other side of the Wheatstone bridge. This known compensation technique removes common mode noise, or background noise, from the signal and focuses the detection on the sample 310 gas.

The apparatus 300 may comprise a controller 104, which may communicate with the detector 316, an ambient temperature sensor 312, and a GC unit temperature sensor 314. The temperature control module 106 may be configured to utilize the temperature sensors 312, 314 to control the temperature of the GC column(s) within the GC unit 308.

Regarding FIGS. 4 through 8B, embodiments with two different switching schemes are described. The first switching scheme is designed to implement the switching between two GC columns GC1, GC2, and embodiments of this scheme are described in FIGS. 4 through 7. The second switching scheme is used to load and unload sampled chemicals on a preconcentration tube 402, and to alternate sample air and clean air to the inlet of GC1. One embodiment of the second switching scheme is detailed in FIGS. 8A and 8B. A given embodiment of the invention may comprise either or both switching schemes. They are illustrated separately to clarify the features of the invention, and it is a mechanical step for one of skill in the art to combine embodiments of the first and second switching schemes in a given embodiment of the invention.

Figure 4:
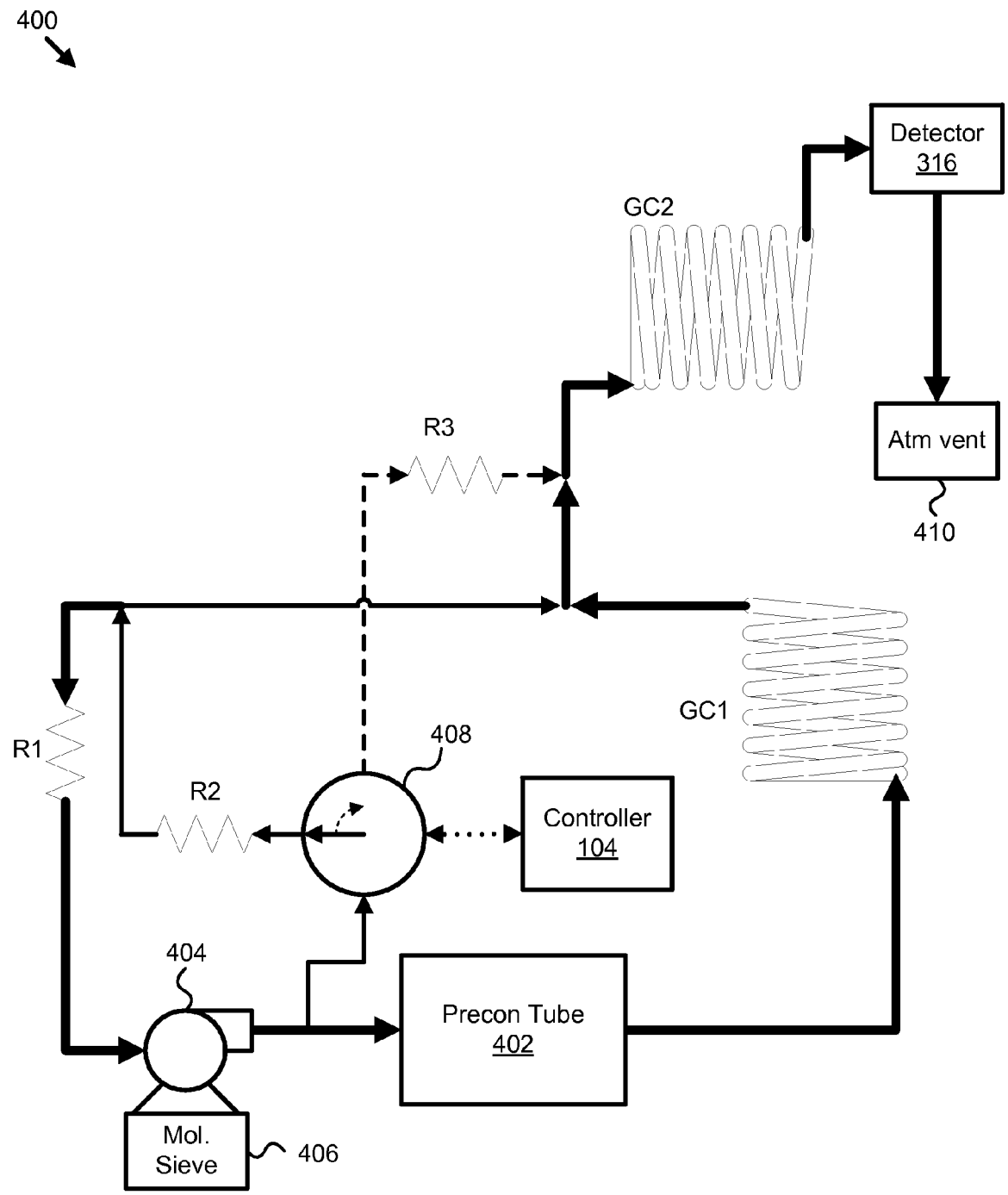
FIG. 4 is a schematic block diagram illustrating one embodiment of an apparatus to control flows to GC columns within a GC sensor in accordance with the present invention.

FIG. 4 is a schematic block diagram illustrating one embodiment of an apparatus 400 to control flows to GC columns within a GC sensor 102 in accordance with the present invention. FIGS. 4 through 8B use the standard convention that where a flow depends upon the position of a valve, a dashed line indicates that the given flow is not occurring with the valve in the position as shown within that Figure.

The apparatus 400 may comprise a first GC column GC1, a second GC column GC2, and a plurality of flow restrictions R1, R2, R3. The flow restrictions R1, R2, R3 may comprise an orifice, controllable valve, inserted microboard with porous substrate, or any other type of configurable pressure drop available in the art. The apparatus 400 may comprise a pre-concentration tube 402, a pump 404, and a molecular sieve 406. The molecular sieve 406 may be configured to remove water and/or other impurities from the gas flow in the apparatus 400, and may be affixed between the pump 404 inlet and outlet. The apparatus 400 shows only the relative flows of GC1 and GC2, while other flows into and out of the apparatus 400 are not shown to avoid cluttering the essential aspects of the embodiment of the invention. Significantly, the introduction of sample 310 gas into the system is not shown.

The apparatus may further comprise a valve 408 configured to direct flow through flow restriction R2 or flow restriction R3. The valve 408 may comprise a solenoid valve. In FIG. 4, the valve 408 is directing flow through restriction R2. The flow through R2 carries the flow out of GC1 into GC2, thereby connecting the GC columns in series, and sending the output of GC1 and GC2 into the detector 316. The detector 316 effluent may vent to the atmosphere 410. In one embodiment, a majority of the flow through R2 may flow through R1 and recycle through the pump 404.

Figure 5:
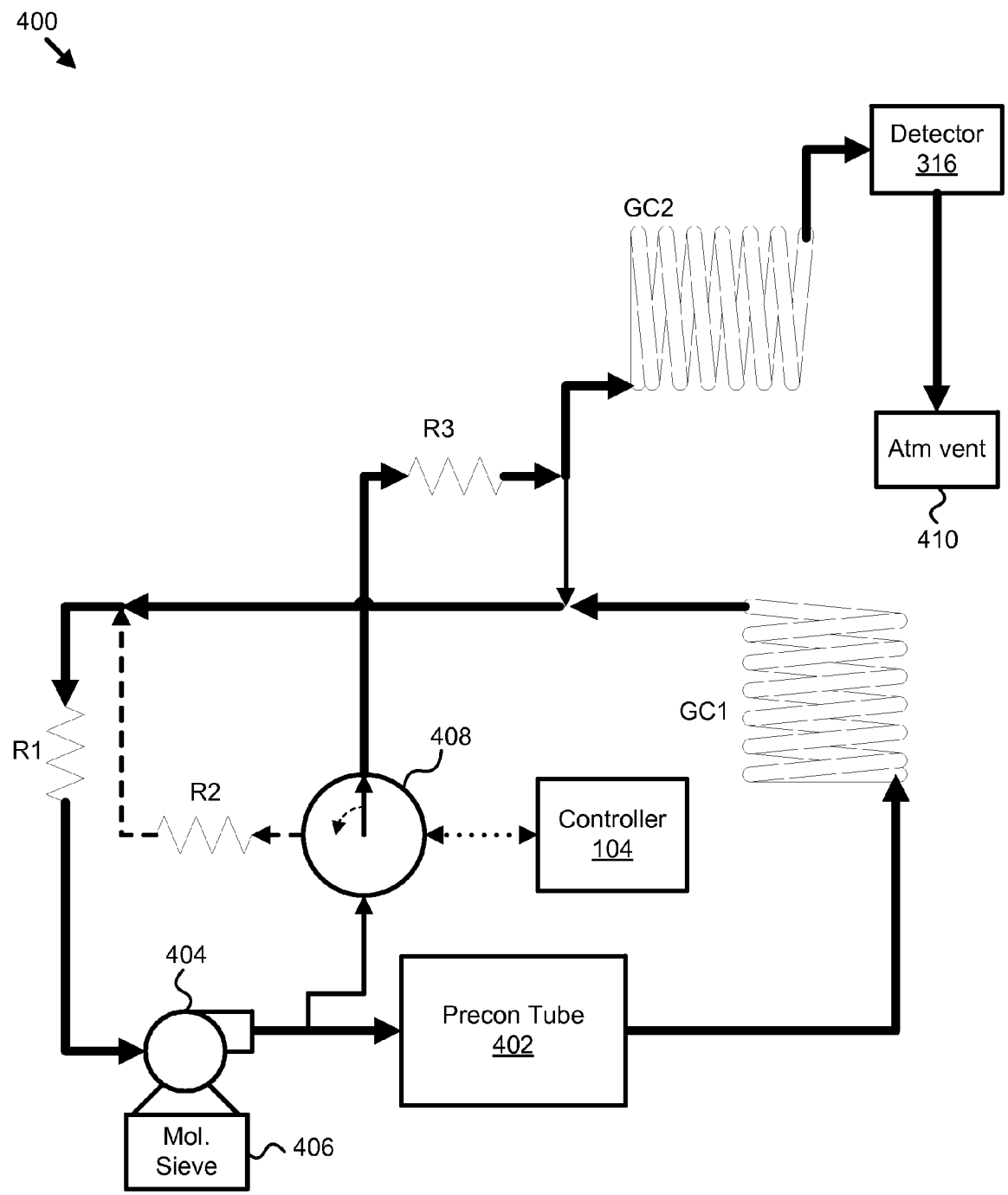
FIG. 5 is a schematic block diagram illustrating one embodiment of an apparatus to control flows to GC columns within a GC sensor in accordance with the present invention.

Referring to FIG. 5, the valve 408 is directing flow through restriction R3. The flow through R3 forces the flow from GC1 away from GC2, and through R1 for venting or recycling. The flow through GC2 is provided by the pump 404. It is apparent from FIGS. 4 and 5 that the apparatus 400 is configured to direct gas flows through the GC columns GC1, GC2 in series or parallel with the use of a solenoid valve 408.

The flow channels of the apparatus 400 may be etched on the surfaces of opposing faces of the sensor 102 body, or they may be machined flow paths within a sensor 102 body.

Figure 6:
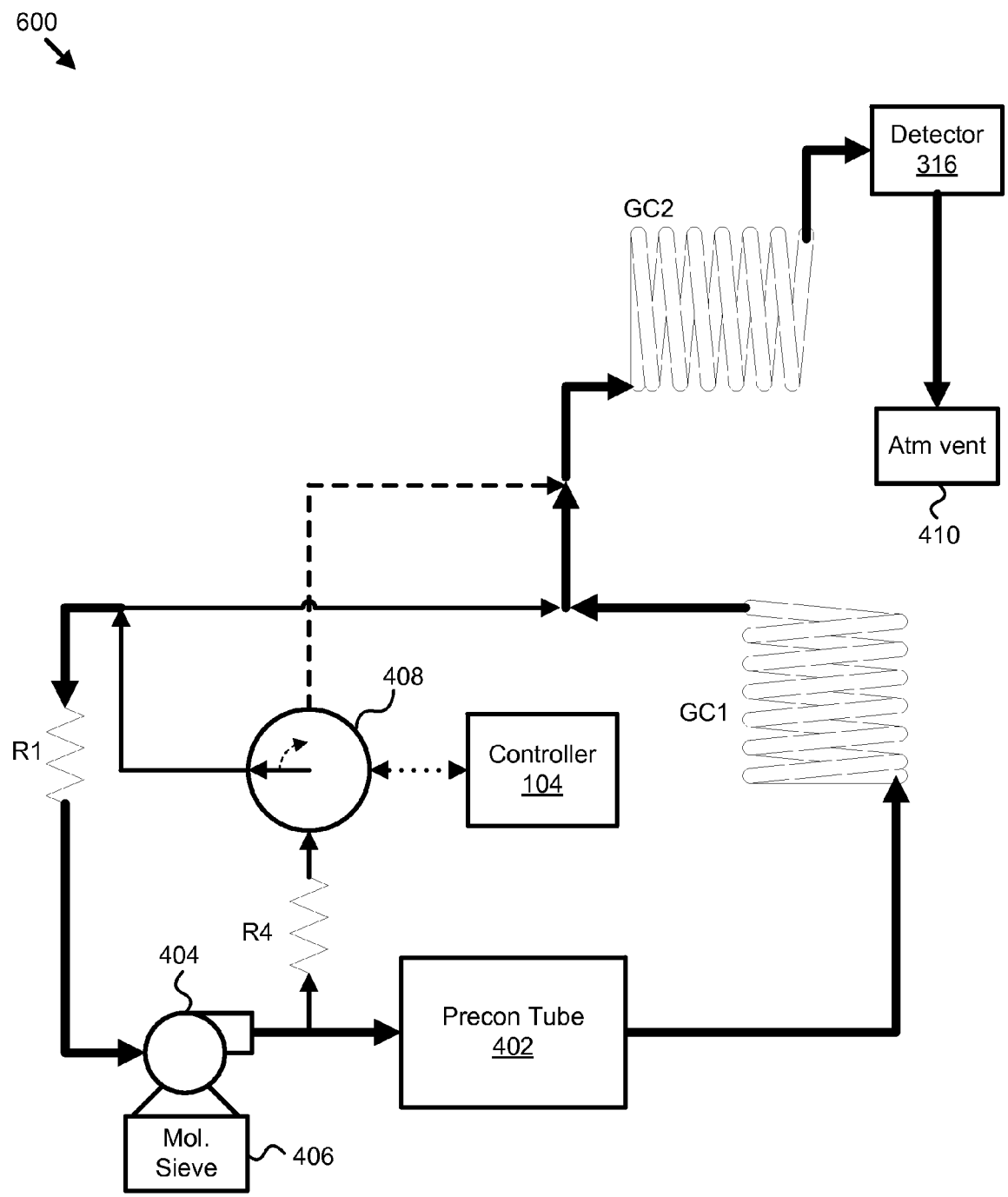
FIG. 6 is a schematic block diagram illustrating an alternative embodiment of an apparatus to control flows to GC columns within a GC sensor in accordance with the present invention.

FIG. 6 is a schematic block diagram illustrating an alternative embodiment of an apparatus 600 to control flows to GC columns GC1, GC2 within a GC sensor 102 in accordance with the present invention. Referring to FIGS. 4 and 5, it is apparent that for the flow rates through GC1 and GC2 to be identical in either position of the valve 408, a condition which may be desirable for the detector 316, the flow restrictions R2, R3 must be identical. Referring back to FIG. 6, those flow restrictions may be replaced with a single restriction R4 before the valve 408 which enforces this condition more effectively. The embodiment of FIG. 6 is otherwise identical to the embodiment of FIG. 5.

Figure 7:
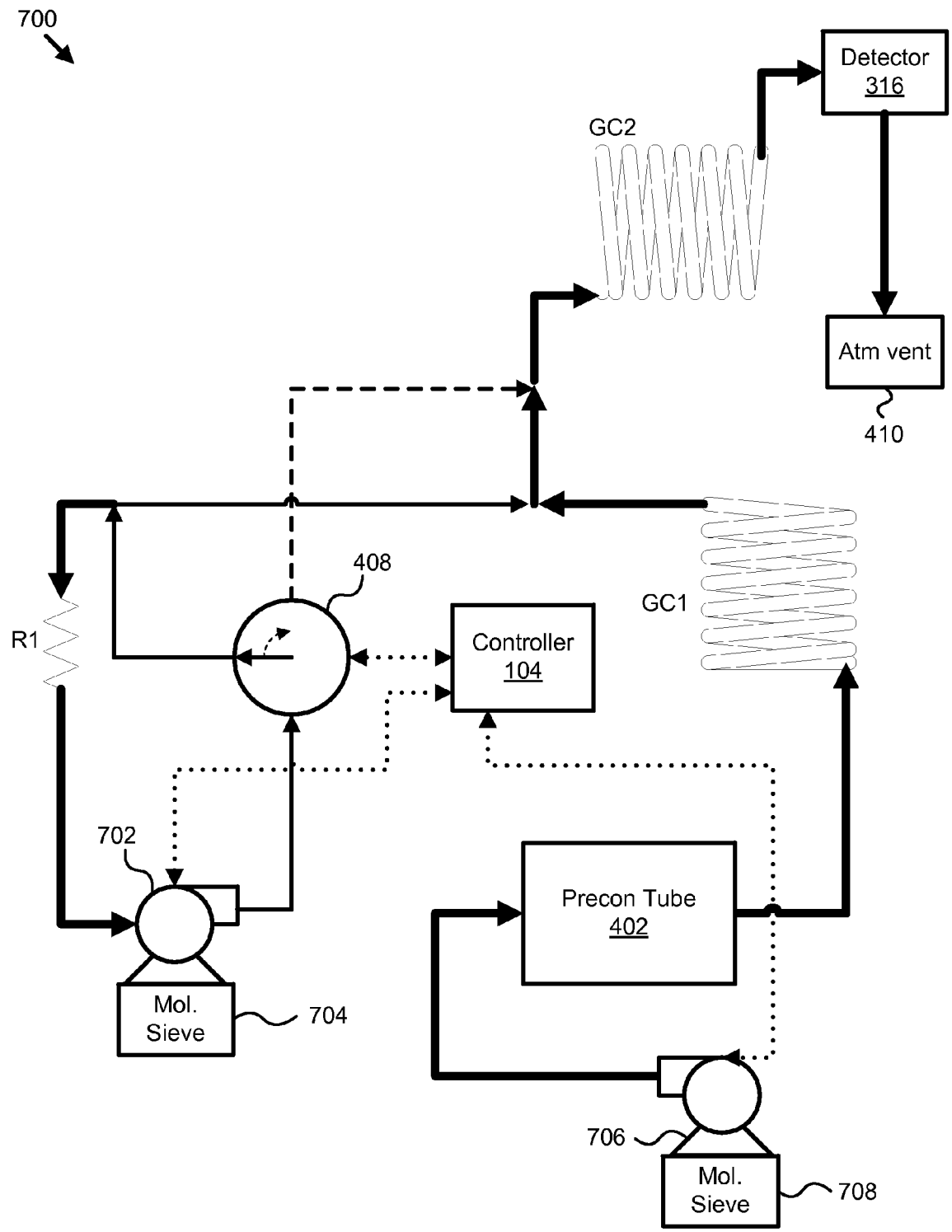
FIG. 7 is a schematic block diagram illustrating an alternative embodiment of an apparatus to control flows to GC columns within a GC sensor in accordance with the present invention.

FIG. 7 is a schematic block diagram illustrating an alternative embodiment of an apparatus 700 to control flows to GC columns GC1, GC2 within a GC sensor 102 in accordance with the present invention. Referring to FIG. 6, it is apparent that for the flow rates through GC1 and GC2 to be identical in either position of the valve 408, the flow restriction R4 must dominate the observed pressure drops for flow throughout the apparatus 600. Referring back to FIG. 7, the single pump 404 is replaced with two pumps 702, 706 which may comprise corresponding molecular sieves 704, 708.

The two pumps 702, 706 may enforce the flow rates through GC1 and GC2 to be identical because the pump 607 controls the flow rate through GC1, and the pump 702 can control the flow rate through GC2. The controller 104 may be configured to control the pumps 702, 704. The restriction R4 may be removed in the apparatus 700, although it may be included (not shown), or lumped with R1 to place the restriction on the low pressure side of the pump 702 instead of the high pressure side if desired. The removal of the restriction R4 may cause a lower nominal pressure in the analysis flow paths of the sensor 102, and thereby increase the sensitivity of the GC sensor 102 to leaks. It is within the skill of one in the art to weigh the increased manufacturing costs to manage leaks, a higher pressure load on the pump 702, and a loss in sensor 102 measurement capability due to unmanaged leaks when determining the inclusion of the restriction R4.

Figure 8A:
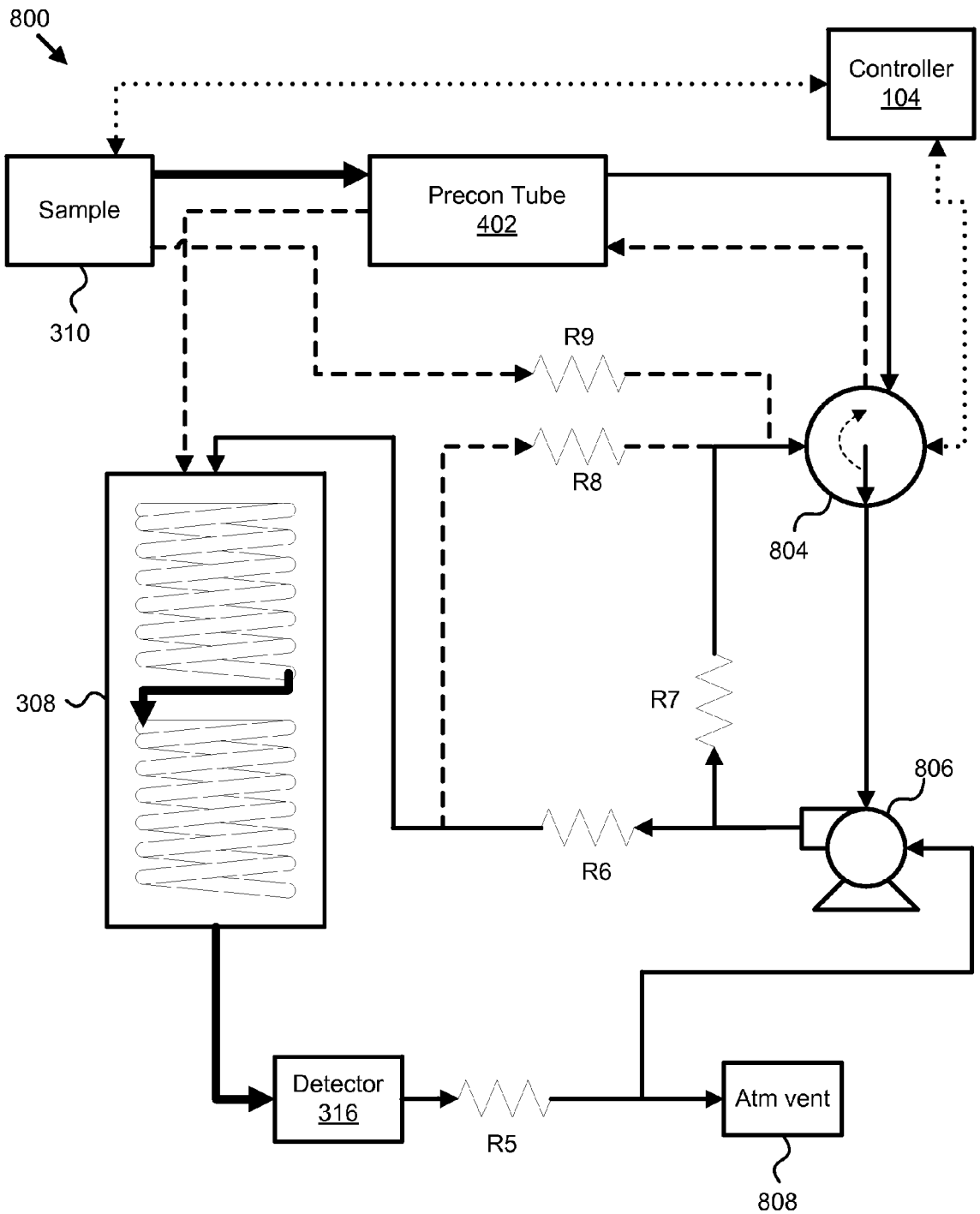
FIG. 8 is a schematic block diagram illustrating one embodiment of an apparatus to control sampling flows within a GC sensor in accordance with the present invention.

FIG. 8A is a schematic block diagram illustrating one embodiment of an apparatus 800 to control sampling flows within a GC sensor 102 in accordance with the present invention. The flow channels of the apparatus 800 may be etched on the surfaces of opposing faces of the sensor 102 body, or they may be machined flow paths within a sensor 102 body. In one embodiment, the flow channels may comprise ceramic or quartz inserts in the analytical (i.e. sample-containing) portions of the sensor 102 to further enhance sealing of the sensor 102 and allow lower concentrations of chemicals in the sample 310 to be detected. Such inserts are estimated to allow detections down into the ppb range. The apparatus 800 may comprise a valve 804 configured to operate the apparatus 800 in the concentration or desorption modes. The apparatus 800 of FIG. 8 is shown in the concentration mode.

In the embodiment of FIG. 8A, the sample 310 is introduced to the preconcentration tube 402 which may adsorb the chemicals of interest. A pump 806 may send gas through a carrier gas flow restriction R6 and to the GC unit 308. Some of the pump 806 effluent may recycle through a desorption flow restriction R7 and return to the pump 806 through the valve 804. The flow may pass from the GC unit 308 to the detector 316, where it may flow through a system flow restriction R5 and to an atmospheric vent 808 or back to the pump 806. Therefore, in one embodiment of the concentration mode, the preconcentration tube 402 is concentrating the sample gas, and the GC unit 308 is receiving clean ambient or carrier gas.

Figure 8B:
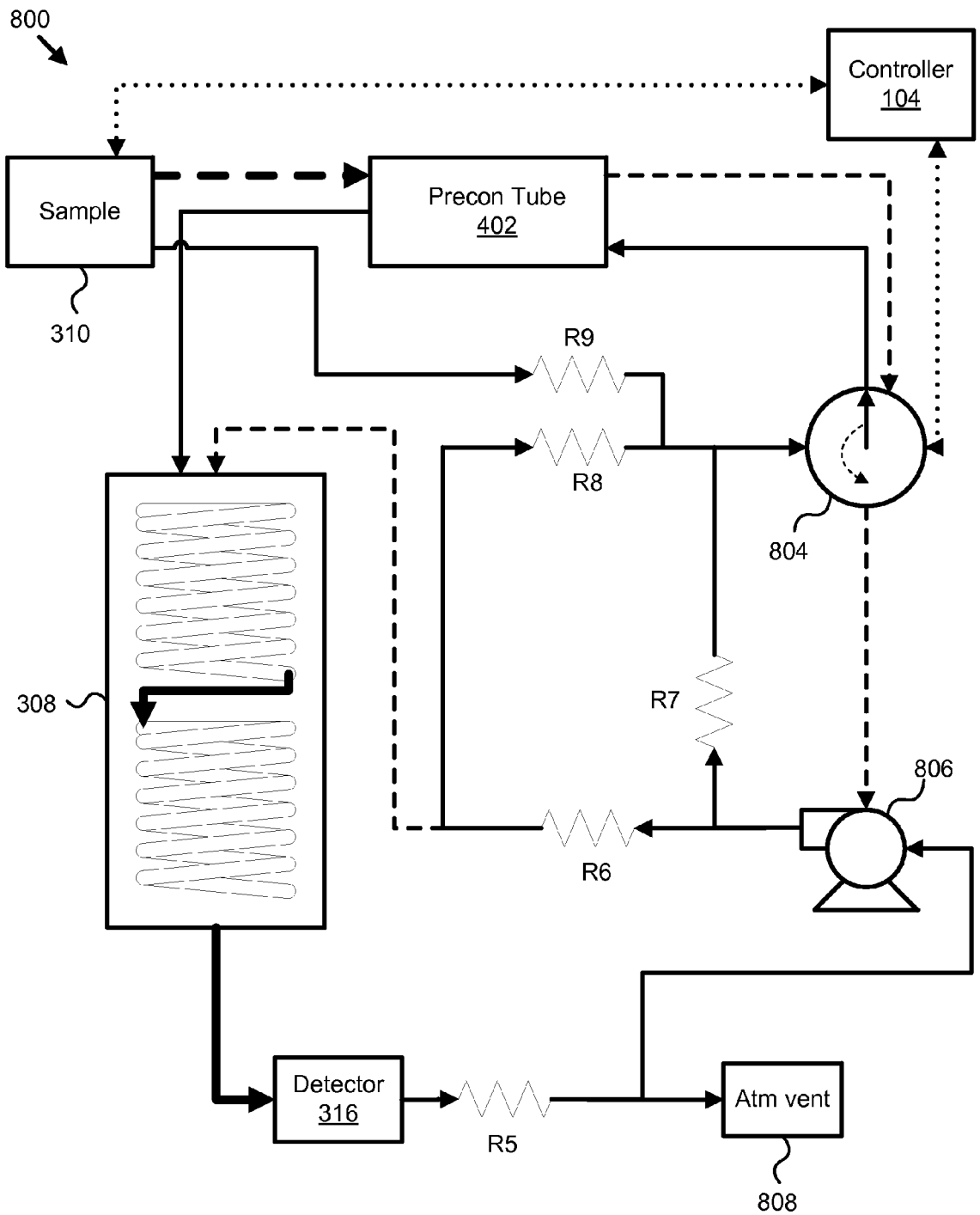

Referring to FIG. 8B, an embodiment is illustrated with the apparatus 800 in the desorption flow regime. The valve 804 is directing flow from the pump 806 reversed through the preconcentration tube 402. Note that the valve 804 has shut down the flow from the pump 806 through the carrier flow restriction to the GC unit 308, although the physical connection of the valve 304 to that flow channel is not shown in FIG. 8B to prevent cluttering the Figure. The sample 310 gas flows through a tube shut flow restriction R9 to the valve 804 and through the preconcentration tube 402, while the pump 806 flow that went to the GC unit 308 is redirected to the valve 804 through a sample flow restriction R8. Therefore, in one embodiment of the desorption mode, the preconcentration tube 402 is desorbing sample gas to the GC unit 308.

Figure 9:
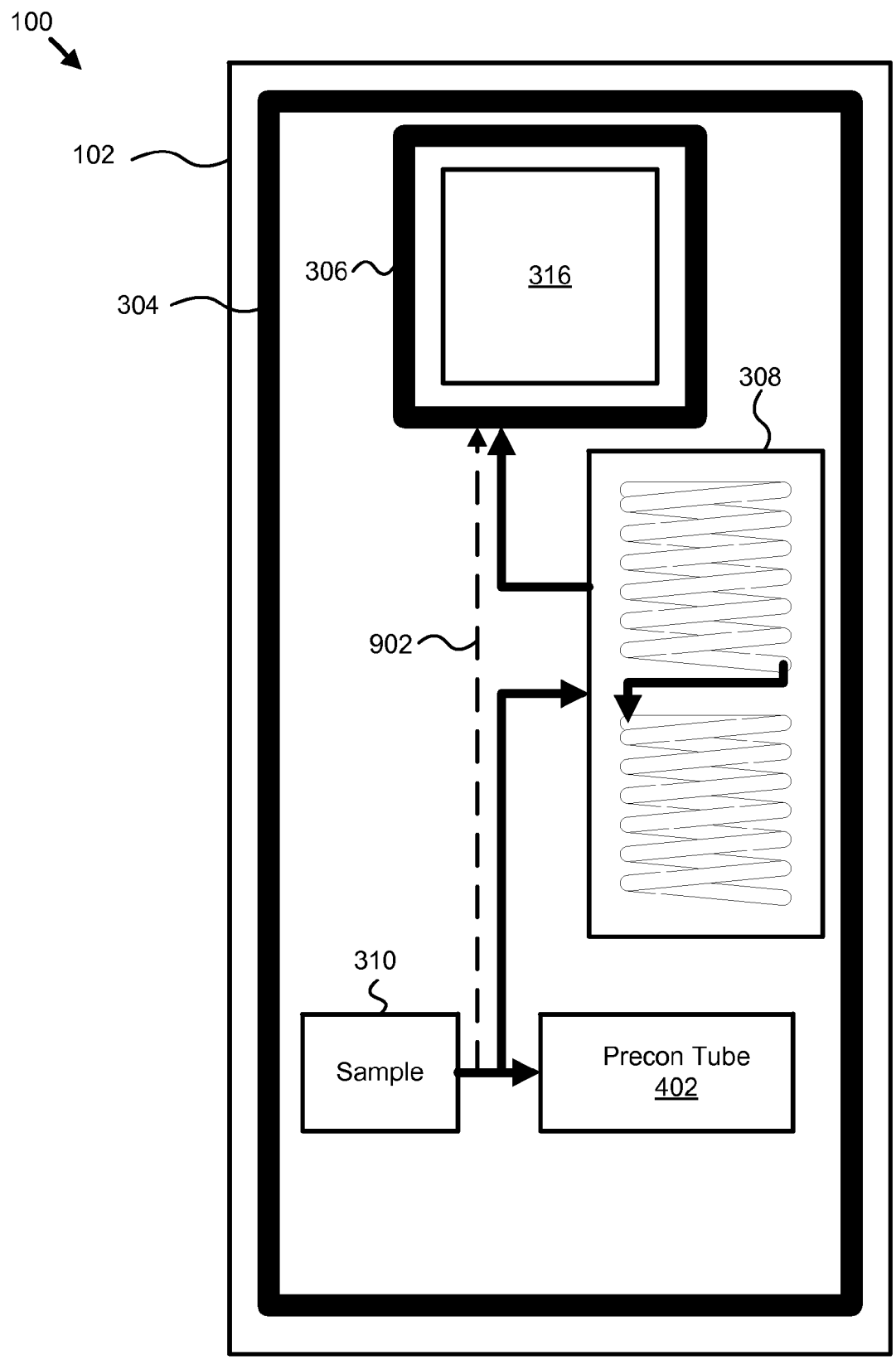
FIG. 9 is a schematic block diagram illustrating one embodiment of an engineered pressure balancing leak in accordance with the present invention.

FIG. 9 is a schematic block diagram illustrating one embodiment of an engineered pressure balancing leak 902 in accordance with the present invention. The detector seal 306 protects the detector 316 from intruding gases which may ruin the sample from the GC unit 308. In one embodiment, the detector seal 306 is considerably more effective if the detector 316 circuit is at an equal pressure with sample 310 channel. If an intentional leak 902 is engineered between the sample 310 flow path and the detector 316, the pressures between the detector 316 and the sensor 102 remain equal. In one embodiment, the leak 902 is engineered in parallel along the sample channel, from the sample 310 introduction through the GC unit 308.

Figure 10:
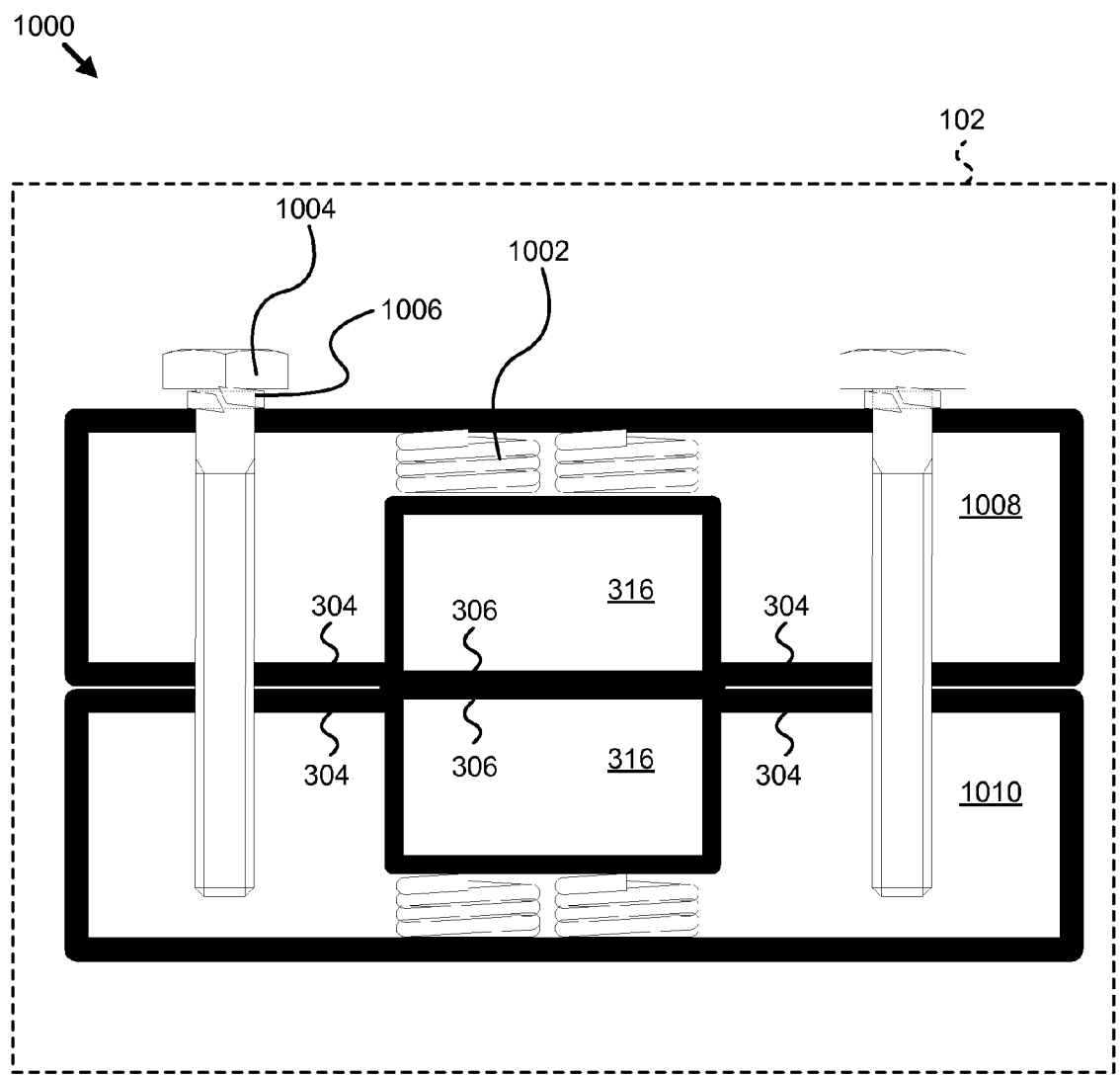
FIG. 10 is a schematic block diagram illustrating one embodiment of an apparatus to seal a GC sensor and detector circuit in accordance with the present invention.

FIG. 10 is a schematic block diagram illustrating one embodiment of an apparatus 1000 to seal a GC sensor 102 and detector circuit 316 in accordance with the present invention. The sensor seal 304 may comprise an adhesive between the faces 1008, 1010 of the sensor 102 body. The faces 1008, 1010 may be pressed together by a plurality of fasteners 1004 with a pressure maintenance mechanism such as a plurality of lock washers 1006.

The detector circuit 316 may be within a cavity in the sensor 102, and may have a sealing surface 306 which may comprise an adhesive between the surfaces 306. The detector seal may further comprise a pressure mechanism 1002 independent from the pressure mechanism 1006 of the sensor seal 304. The pressure mechanism 1002 may comprise one or more springs configured to apply pressure to the detector circuit 316 faces 306 to keep them sealed.

Figure 11:
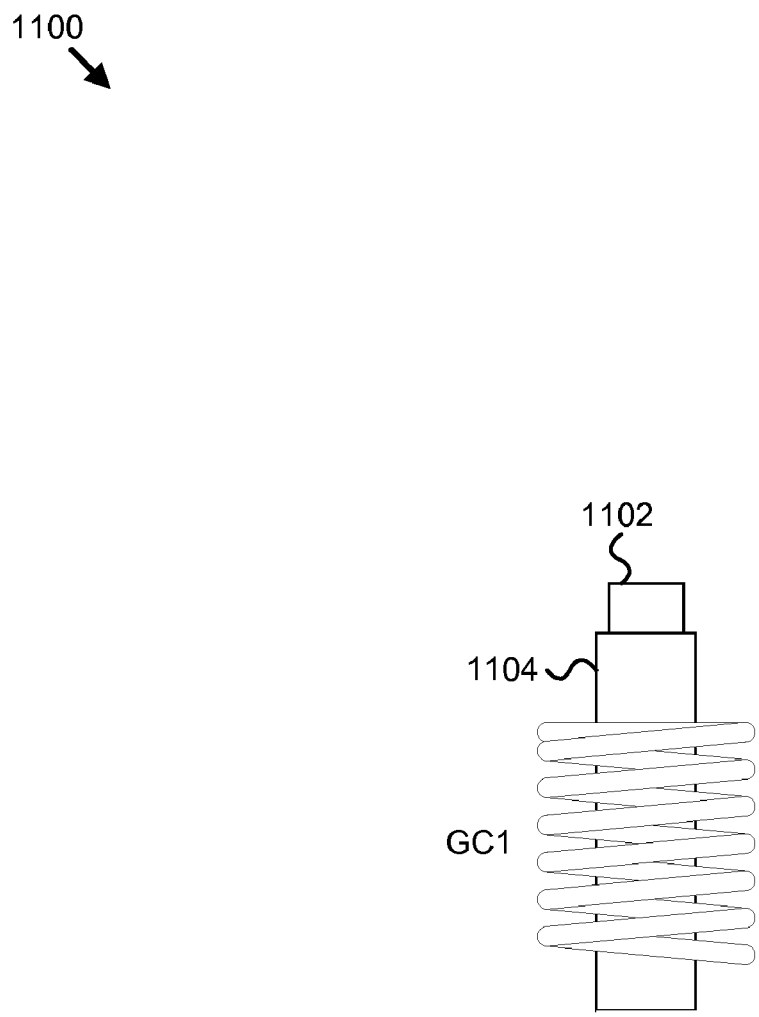
FIG. 11 is a schematic block diagram illustrating one embodiment of an apparatus to uniformly heat a GC column in accordance with the present invention.

FIG. 11 is a schematic block diagram illustrating one embodiment of an apparatus 1100 to uniformly heat a GC column GC1 in accordance with the present invention. The apparatus 1100 may comprise a heating element 1102. The heating element 1102 may comprise a heating element 1102 with a higher wattage rating than the required wattage to heat the GC column GC1 from the lowest predicted ambient temperature 202 to the highest GC target temperature 206. Such a design allows the heating element 1102 to provide the heat required for the sensor at a lower current and heating element 1102 temperature than a minimally specified heating element would. Such a design minimizes the potential for heat spikes and non-uniformity throughout the GC column GC1.

The apparatus 1100 may further comprise insulation 1104 between the heating element and the GC column GC1. The insulation 1104 further reduces the occurrence of temperature variability induced in the GC column GC1 by the heating element 1102.

Figure 12A:
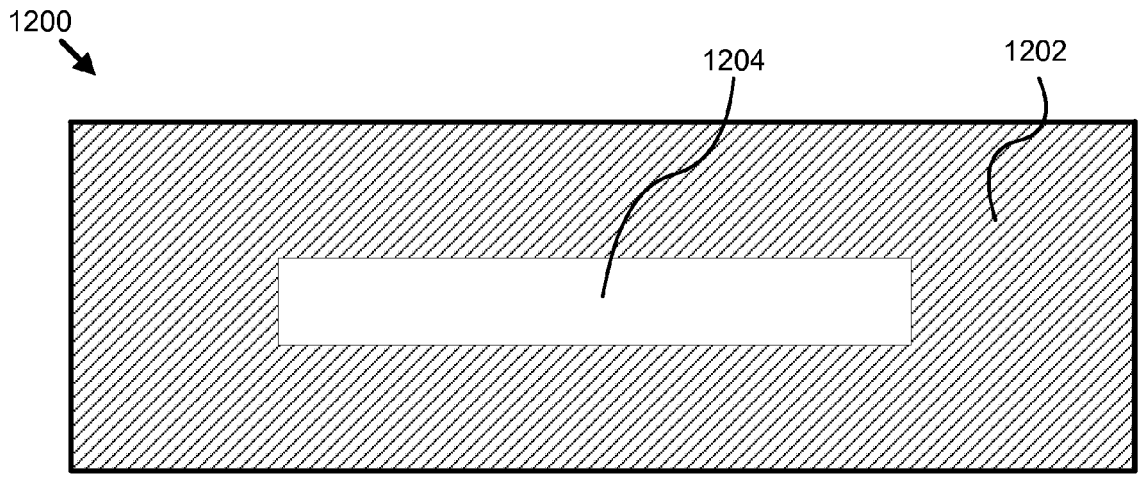
FIG. 12A is a schematic block diagram illustrating one embodiment of a slot for packing a preconcentration material in accordance with the present invention.

FIG. 12A is a schematic block diagram illustrating one embodiment 1200 of a slot 1204 machined into the sensor body 1202 for packing a preconcentration material in accordance with the present invention. The slot 1204 may be machined vertically into the sensor body 1202 and the apparatus 1200 may be packed vertically. Further, the slot 1204 may comprise a slot machined into the sensor body 1202, with a tube inserted into the slot, wherein the apparatus 1200 is packed into the tube.

Figure 12B:
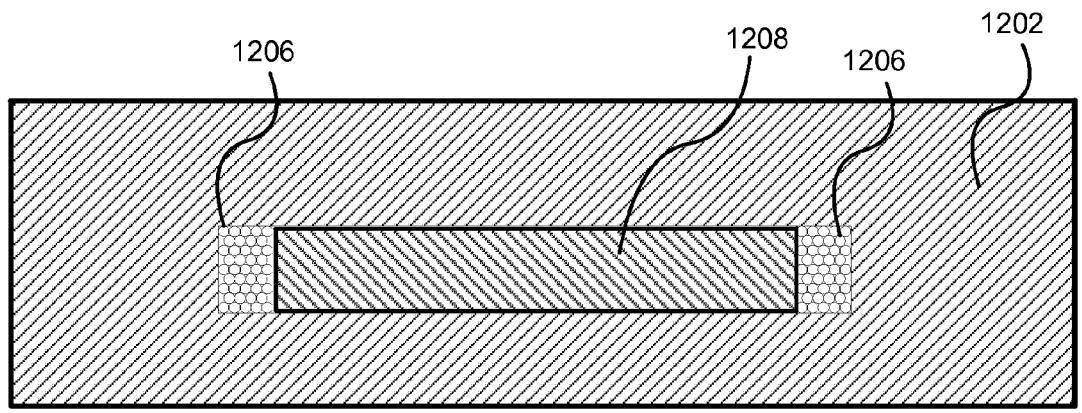
FIG. 12B is a schematic block diagram illustrating one embodiment of a packed preconcentration material in accordance with the present invention.
Figure 12C:
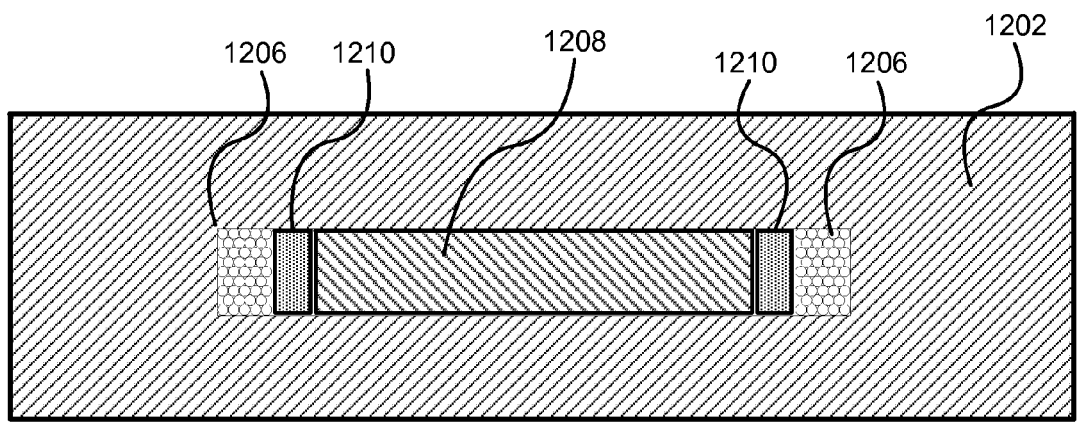
FIG. 12C is a schematic block diagram illustrating an alternative embodiment of a packed preconcentration material in accordance with the present invention.

Referring to FIG. 12B, the slot may be packed by inserting a slurry comprising microspheres and adhesive to form a uniformly porous plug 1206 at a first end of the slot 1204, and packing in the preconcentration material 1208. The apparatus 1200 may be completed by inserting a slurry to form a uniformly porous plug 1206 at a second end of the slot 1204. Referring to FIG. 12C, it may be desirable to offset the preconcentration material 1208 from the adhesive slurry 1206. Therefore, the apparatus 1200 of FIG. 12C shows the preconcentration material 1208 separated from the adhesive slurry 1206 by a pair of offset rods 1210 configured to offset the preconcentration material 1208 the desired distance.

The adhesive slurry may comprise glass microspheres. The adhesive may comprise an epoxy glue comprising 10% or less by weight of the slurry. The glass-glue mixture provides a consistent pressure drop once evenly mixed.

Figure 13:
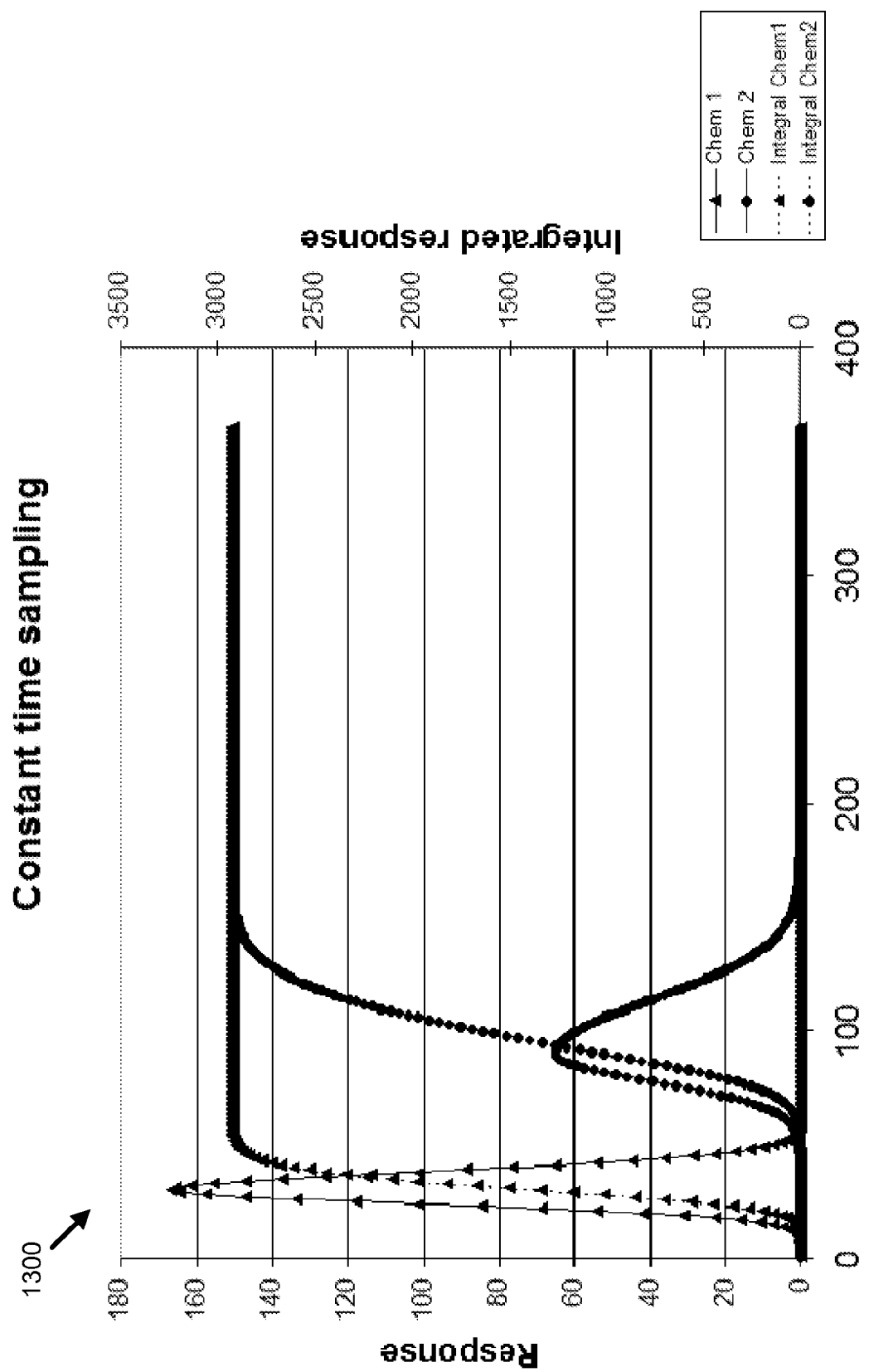
FIG. 13 is an illustration of sampling data in accordance with the present invention.

FIG. 13 is an illustration of sampling data 1300 shown in constant time, in accordance with the present invention. The example data labeled Chem 1 may be a typical elution peak for a relatively fast-eluting chemical, and the example data labeled Chem 2 may be a typical elution peak for a relatively slow-eluting chemical. Note that the time scale for FIG. 13 is relative only, and that the differences between the fast-eluting and slow-eluting chemicals are compressed to demonstrate the similarity effect and relative peak shapes. In practice, chemicals with elution peak widths that vary as much as those shown in FIG. 13 will often, but not necessarily, exhibit much greater separation in the time axis.

The fast eluting chemical may comprise a sharp peak as shown, and a relatively small number of sample points. The slow eluting chemical may comprise a flattened peak as shown, and a relatively large number of sample points. The area under the peaks is similar in the examples, as evidenced by the similar final values of the integration curves, indicating that these two chemicals were in the sample at approximately the same concentrations. The differences in the peak widths and the number of samples in each peak may complicate the use of a modified Z-transform in analyzing GC sensor 102 signals.

Figure 14:
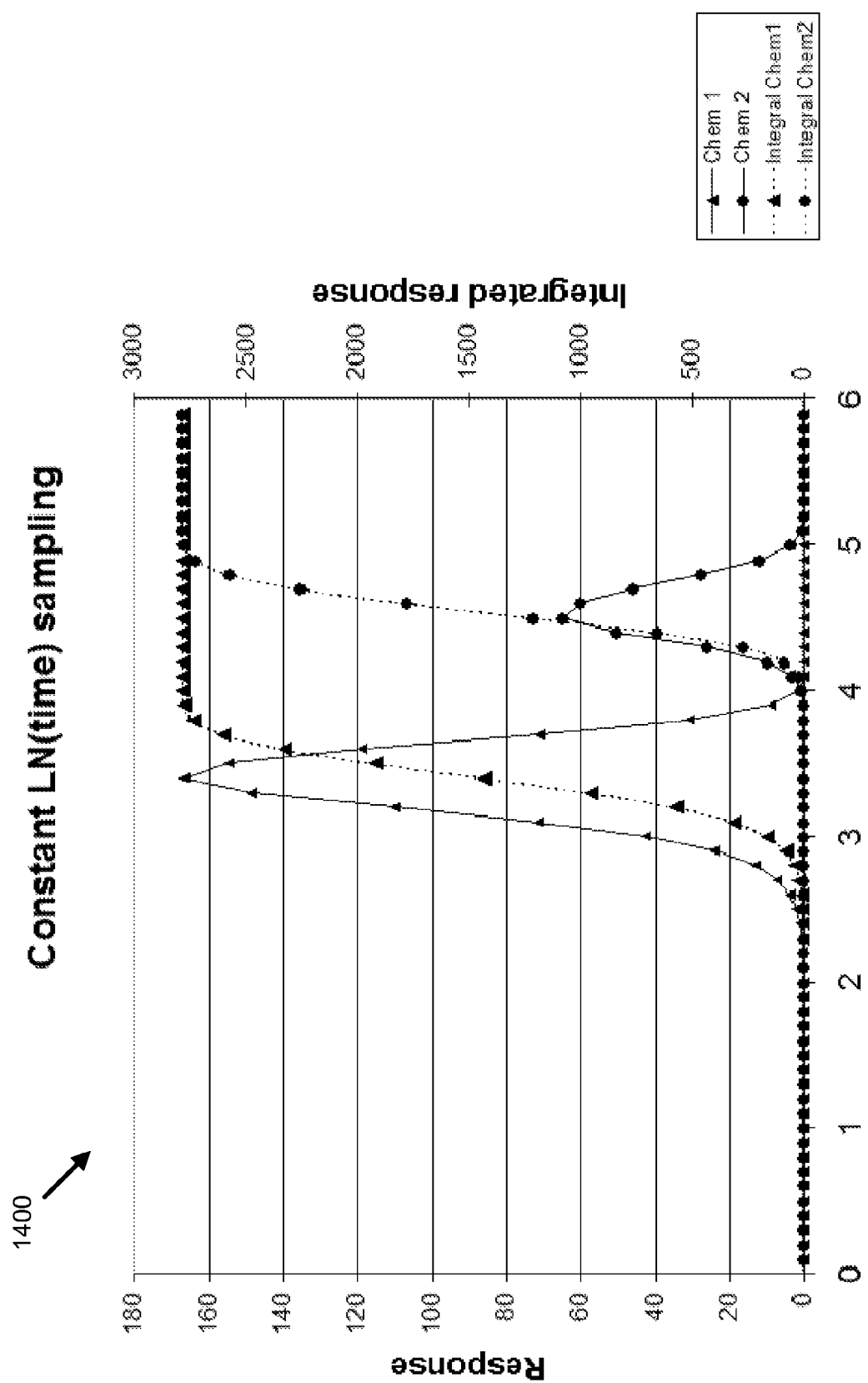
FIG. 14 is an illustration of alternative sampling data in accordance with the present invention.

FIG. 14 is an illustration of sampling data 1400 shown in constant log time, in accordance with the present invention. For purposes of illustration, the same example data from FIG. 13 is shown in FIG. 14, and therefore the time axis differences between the fast and slow eluting chemicals may likewise be compressed in FIG. 14. The fast eluting chemical may comprise a sharp peak as shown. The slow eluting chemical may comprise a similarly shaped peak in constant log time. The peaks for the fast and slow eluting chemicals in FIG. 14 may exhibit similar numbers of sample points within each peak. Note that the integral curves in FIG. 14 are generated with a rectangular estimate, and that close observation of the integral curves in FIG. 14 illustrates that although the fast and slow eluting chemicals had the same area under the curve in constant time sampling, they are not at exactly the same area under the curve in constant log-time sampling, although the introduced error is small.

Figure 15:
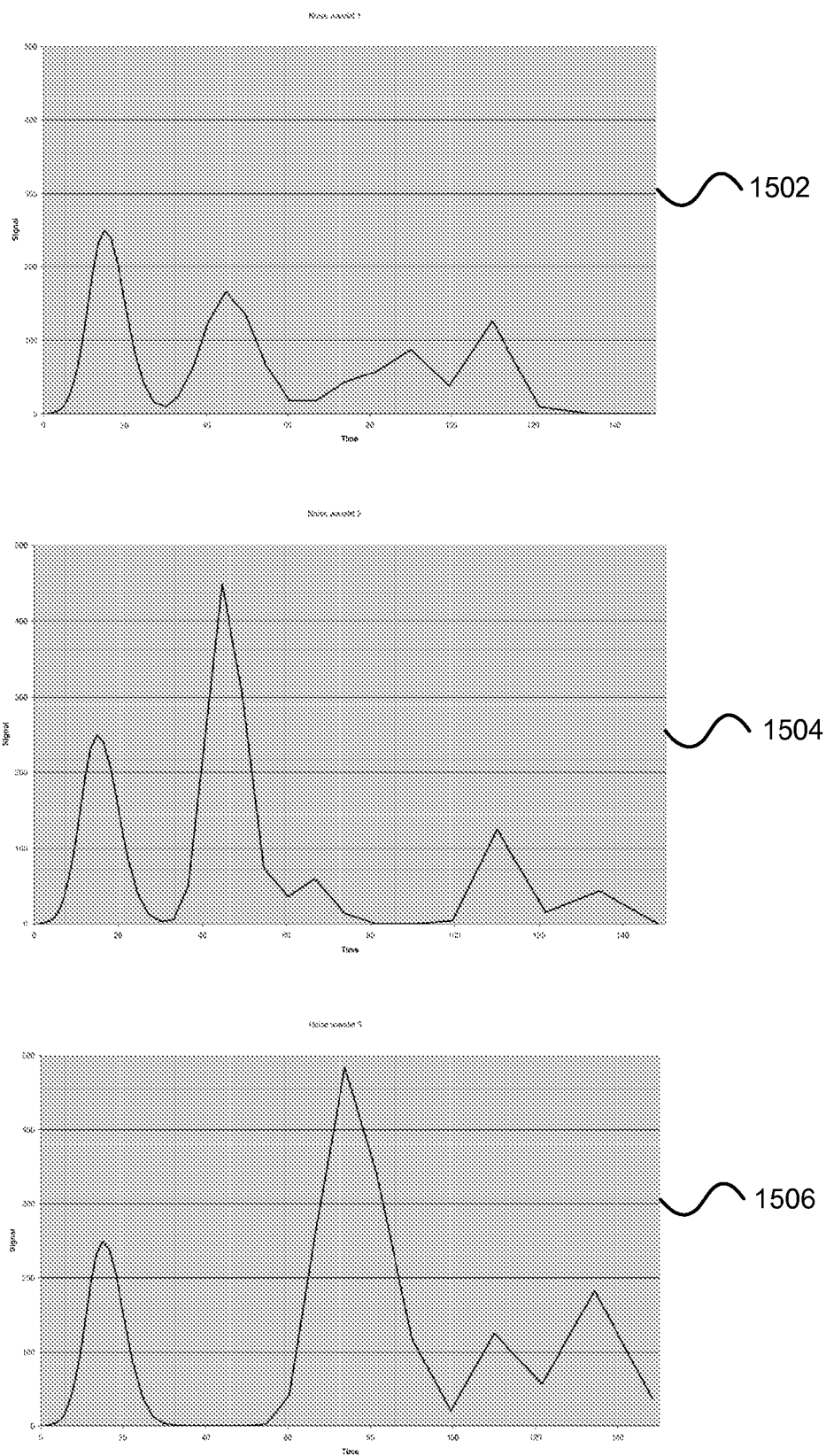
FIG. 15 is an illustration of sampling data adjusted with a plurality of noise wavelets in accordance with the present invention.

FIG. 15 is an illustration of sampling data adjusted with a plurality of noise suppression methods in accordance with the present invention. The first data set 1502 may show a data set adjusted by a first noise suppression method, the second data set 1504 may show a data set adjusted by a second noise suppression method, and the third data set 1506 may show a data set adjusted by a third noise suppression method. In one embodiment, the noise-filtering module 116 may label a peak at about 15 time units as data because this peak occurs in all three sets 1502, 1504, 1506. The noise-filtering module 116 may label peaks at about 45, 65, 75, 90, and 130 time units as noise because these peaks appear on only some of the sets 1502, 1504, 1506. Further, the noise-filtering module 116 may label a peak at about 115 time units as data because this peak occurs in all three data sets 1502, 1504, 1506. The noise suppression methods may be noise suppression wavelets.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 16:
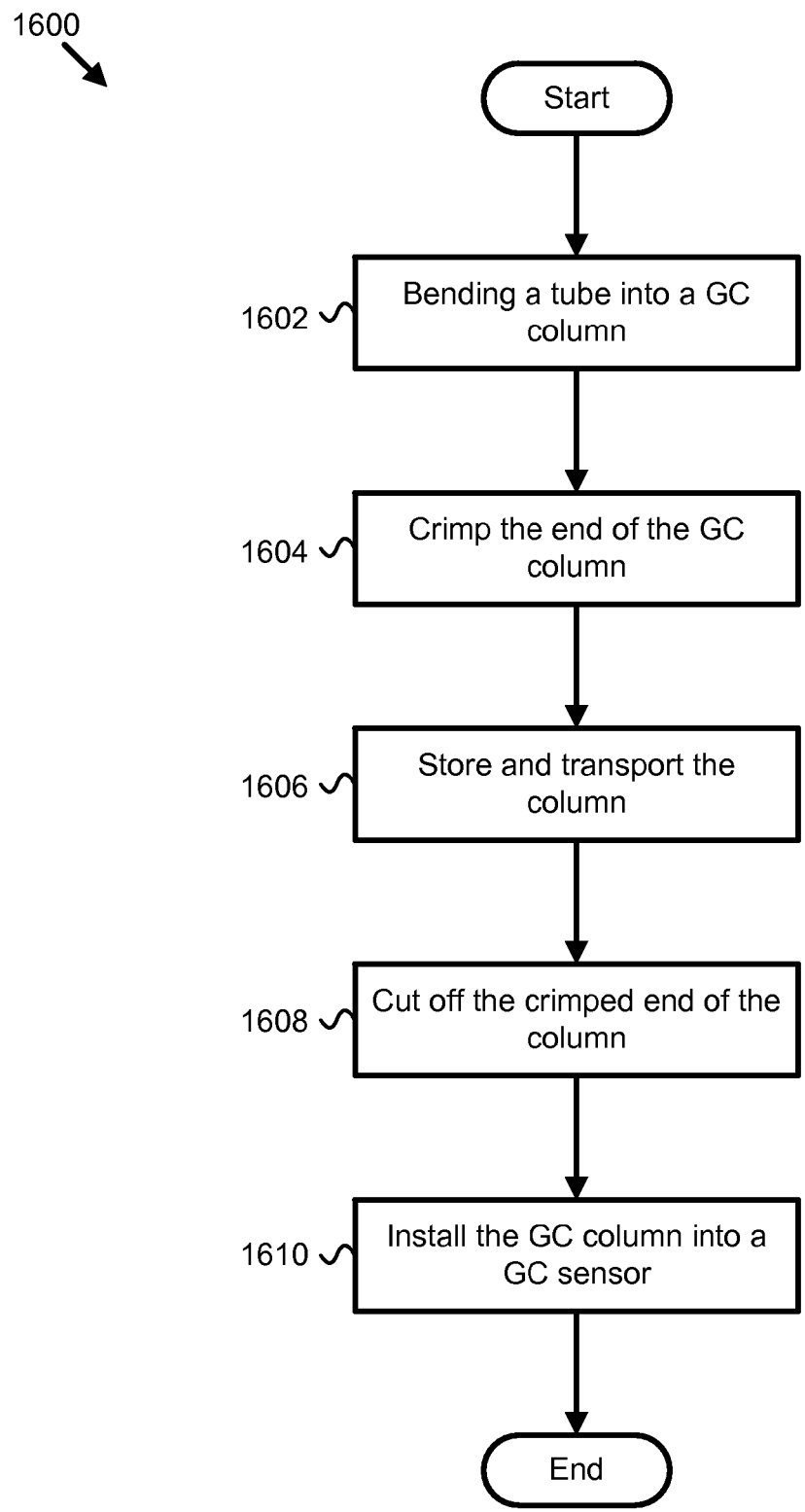
FIG. 16 is a schematic flow diagram illustrating one embodiment of a method to manufacture a GC column in accordance with the present invention.

FIG. 16 is a schematic flow diagram illustrating one embodiment of a method 1600 to manufacture a GC column GC1, GC2 in accordance with the present invention. The method 1600 may be performed with a torsion spring making machine configured to manage materials of the diameter of the GC column GC1, GC2. The method 1600 may begin with bending 1602 a tube of slightly longer than the desired GC column length into a GC column GC1, GC2. Then, the tube may be crimped 1604 at the ends to facilitate maintaining tube cleanliness during storage 1606 and/or transport 1606 of the column GC1, GC2. Then method 1600 may continue with a practitioner cutting 1608 off the ends of the column GC1, GC2 and installing 1610 the column GC1, GC2 into a GC sensor 102.

Figure 17:
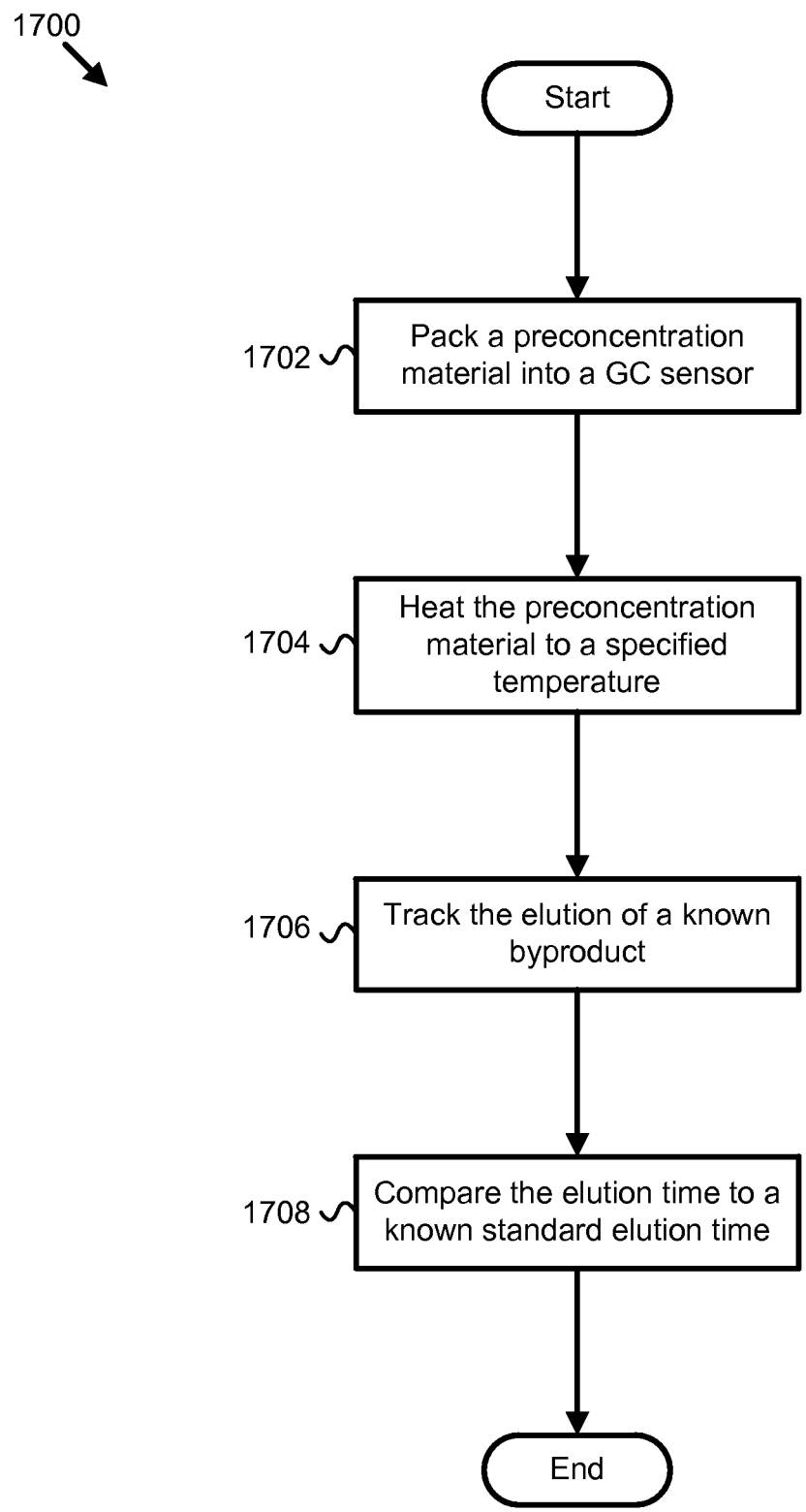
FIG. 17 is a schematic flow diagram illustrating one embodiment of a method to utilize an internal standard chemical in a GC sensor in accordance with the present invention.

FIG. 17 is a schematic flow diagram illustrating one embodiment of a method 1700 to utilize an internal standard chemical in a GC sensor 102 in accordance with the present invention. The method 1700 may begin with packing 1702 a preconcentration material 1208 into a GC sensor. The preconcentration material 1208 may comprise a known material, for example Tenax, that releases a known byproduct at a set temperature. The method 1700 may proceed with heating 1704 the preconcentration material 1208 to a specified temperature at which the known byproduct is released. The controller 104 may then track 1706 the elution of the known byproduct, and compare 1708 the elution time to a known standard elution time according to the temperature of the GC columns GC1, GC2.

Figure 18:
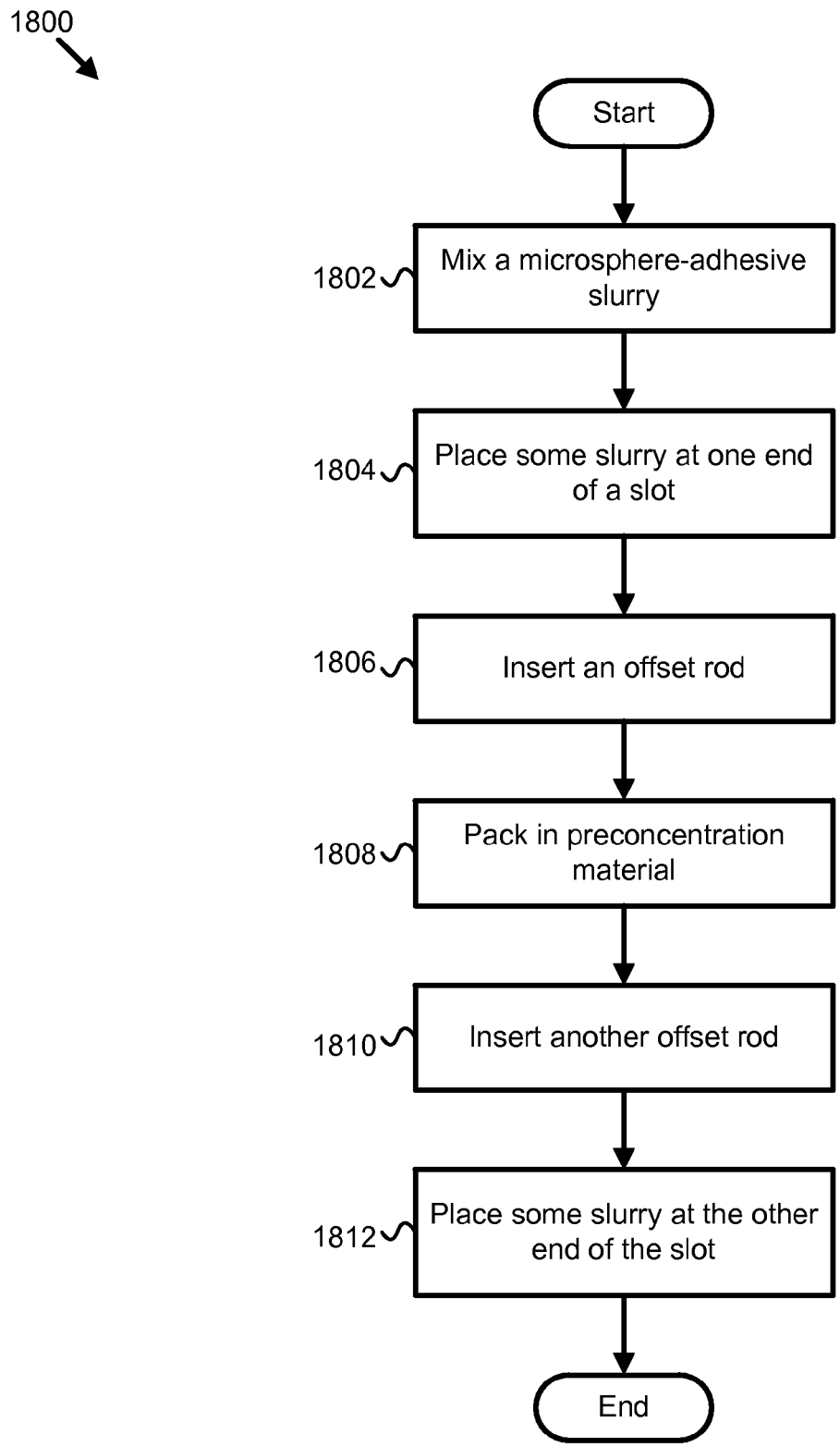
FIG. 18 is a schematic flow diagram illustrating one embodiment of a method to pack a preconcentration material in accordance with the present invention.

FIG. 18 is a schematic flow diagram illustrating one embodiment of a method 1800 to pack a preconcentration material 1208 in accordance with the present invention. The method 1800 may begin with a practitioner mixing 1802 a microsphere-adhesive slurry and placing 1804 some of the slurry at one end of a slot 1204. The practitioner may then insert 1806 an offset rod into the slot to position a preconcentration material in the slot 1204. The practitioner may then pack 1808 a preconcentration material into the slot, and insert 1810 another offset rod into the slot. The practitioner may then fill the slot 1204 with microsphere-adhesive slurry to complete the packing of the preconcentration material.

Figure 19:
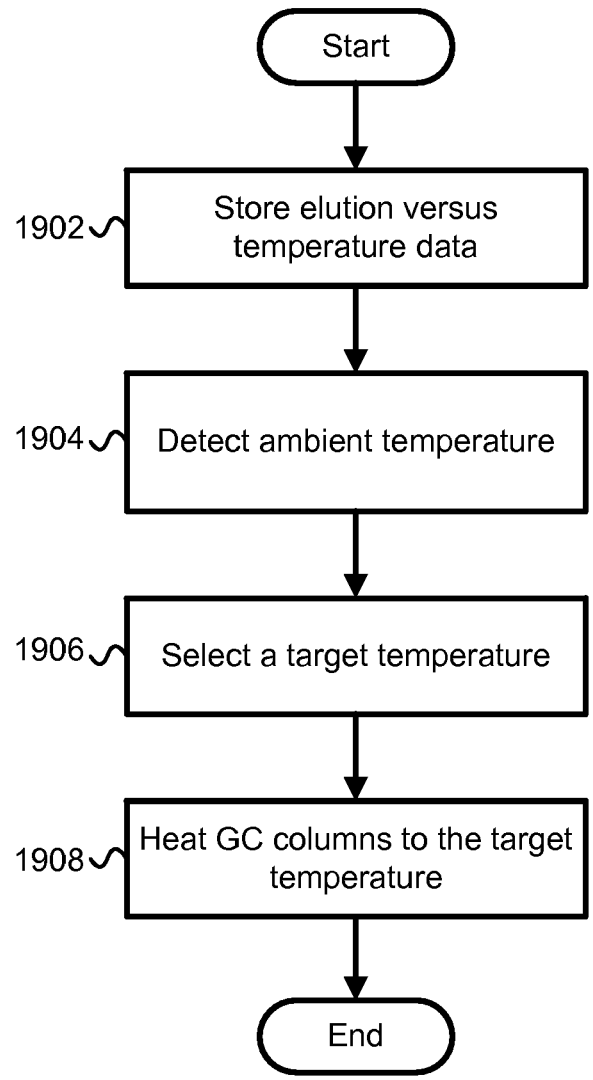
FIG. 19 is a schematic flow diagram illustrating one embodiment of a method to control the temperature of a GC column in accordance with the present invention.

FIG. 19 is a schematic flow diagram illustrating one embodiment of a method 1900 to control the temperature of a GC column GC1, GC2 in accordance with the present invention. The method 1900 may begin 1902 with the controller storing 1902 a set of elution versus temperature data for a number of chemicals of interest. The temperature control module 106 may be configured to detect 1904 the ambient temperature 202, and to select 1906 a target temperature 206 for the GC column(s) based on the ambient temperature 202 and the elution versus temperature data 204. The temperature control module 106 may be further configured to heat 1908 the GC column(s) GC1, GC2 to the target temperature 206.

Figure 20:
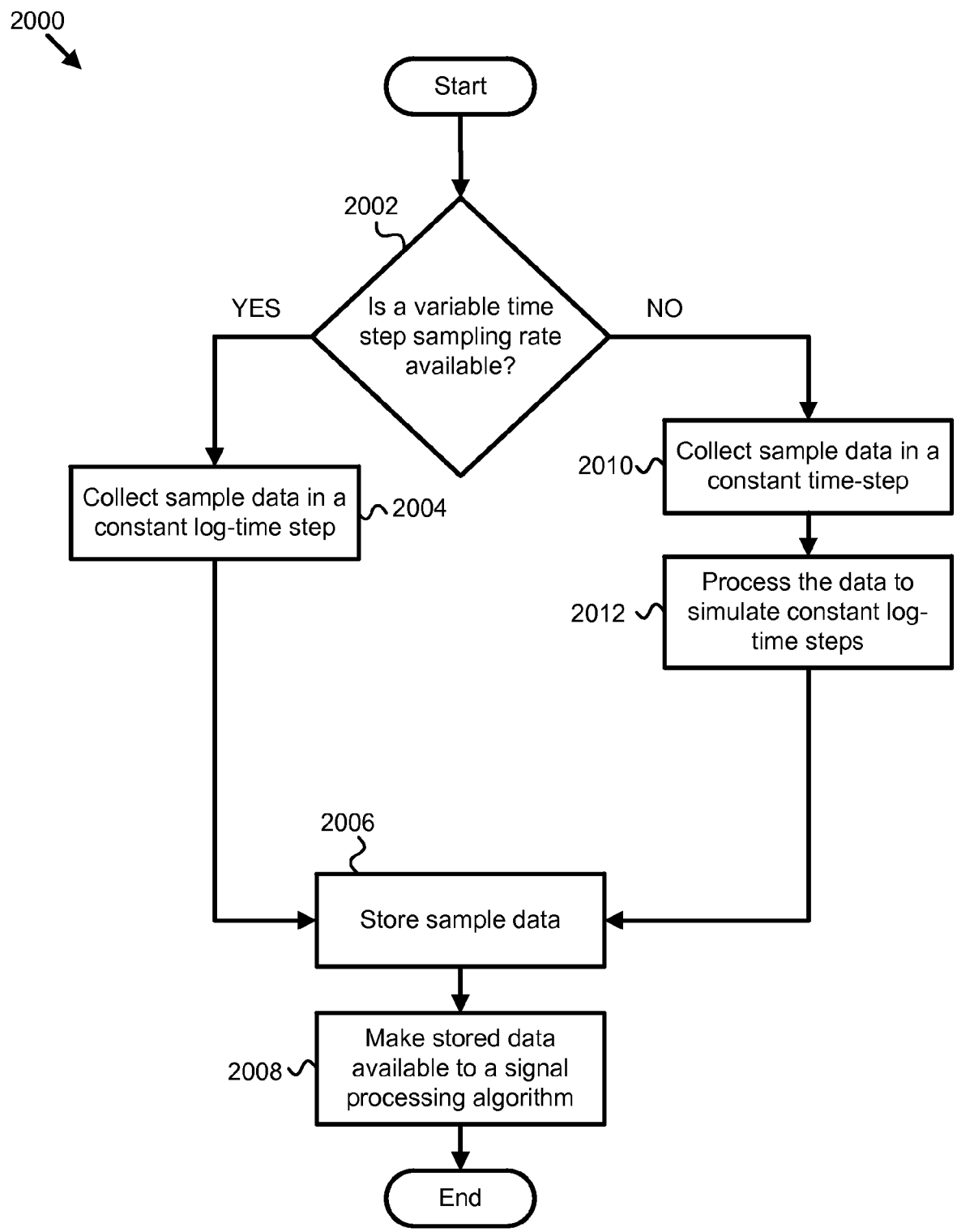
FIG. 20 is a schematic flow diagram illustrating one embodiment of a similarity sequencing sample data acquisition method in accordance with the present invention.

FIG. 20 is a schematic flow diagram illustrating one embodiment of a similarity sequencing sample data acquisition method 2000 in accordance with the present invention. The method 2000 may begin with the similarity sequencing module 112 determining 2002 whether a variable time step sampling rate is available. Where variable time step sampling is available, the similarity sequencing module 112 may collect 2004 data in a constant log-time step, wherein each data point proceeds at the time value t, where:

$$t = A * e^{k*s}$$   Equation 3.

In Equation 3, s is the sample number to be taken, and t is the normal time at which the sample is taken. The value k determines the distance between sample increments, while the value A is used to define the time at which the first sample is taken. For example, the value k may be 0.2, and A may be 1. In the example, the first sample is taken at approximately 1.22 seconds, the second sample at 1.49 seconds, and another sample is taken at each 0.2 log-seconds. In the example, the $20^{th}$ sample would be taken at about 54.6 seconds.

Where variable time step sampling is not available, the similarity sequencing module 112 may collect 2010 data in a constant normal-time step, and process 2012 the data to simulate constant log-time steps.

Note that in the example presented in FIG. 20, constant log-time samples are utilized for the similarity sequencing scheme. In many embodiments, the use of constant log-time samples have been found to work well. However, any similarity sequencing scheme that yields similar peak shapes for a broad range of elution times is contemplated within the scope of the present invention. For example, a polynomial time step sequence can be fit to a fast-eluting and a slow-eluting chemical, providing a similarity sequencing scheme that could be utilized in the method 2000. In the example, the step 2004 would comprise collecting the sample data in a time step sequence according to the polynomial time step sequence. In the example, where variable time step sampling rates are not available, the step 2012 would comprise processing the data to simulate the polynomial time step sequence. It is a mechanical step for one of skill in the art to transform constant time-step data into an arbitrary similarity sequencing scheme based upon the disclosures herein.

The method 2000 may proceed with the similarity sequencing module 112 storing 2006 the sample data, and the controller 104 may make 2008 the stored data available to a signal processing algorithm on the signal processing module 114.

Figure 21:
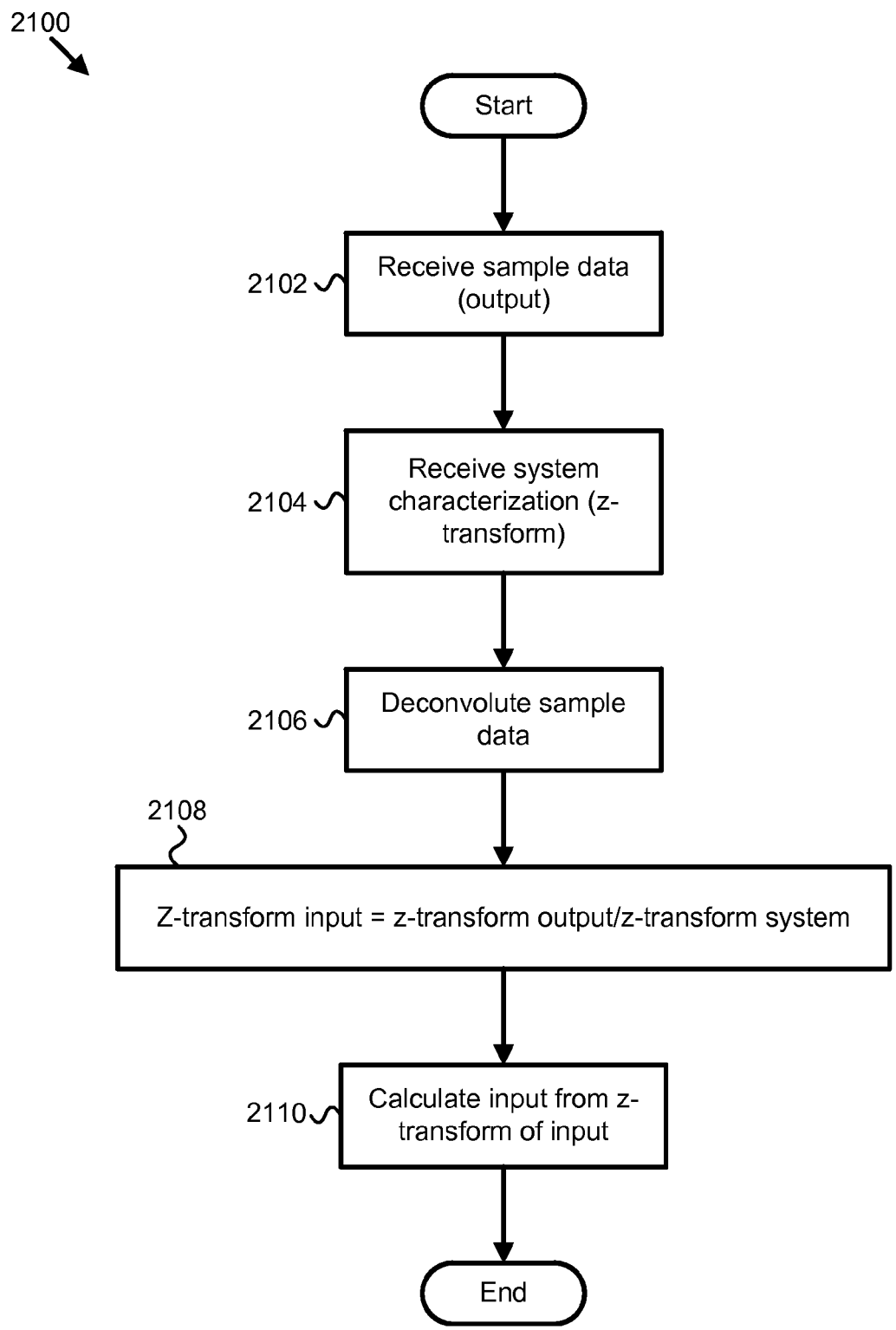
FIG. 21 is a schematic flow diagram illustrating one embodiment of a method for analyzing sampling data in accordance with the present invention.

FIG. 21 is a schematic flow diagram illustrating one embodiment of a method 2100 for analyzing sampling data in accordance with the present invention. The method 2100 may begin with the signal processing module 114 receiving 2102 sample data 216 which may be sequenced by the similarity sequencing module 112. The signal processing module 114 may receive 2104 a system characterization which may comprise a Z-transform transfer function of the system 100. The signal processing module 114 may deconvolute 2106 the sample data 216 with the largest polynomial division that does not produce a negative response and induce instability. The signal processing module 114 may then determine the input signal according to Equation 2.

Figure 22:
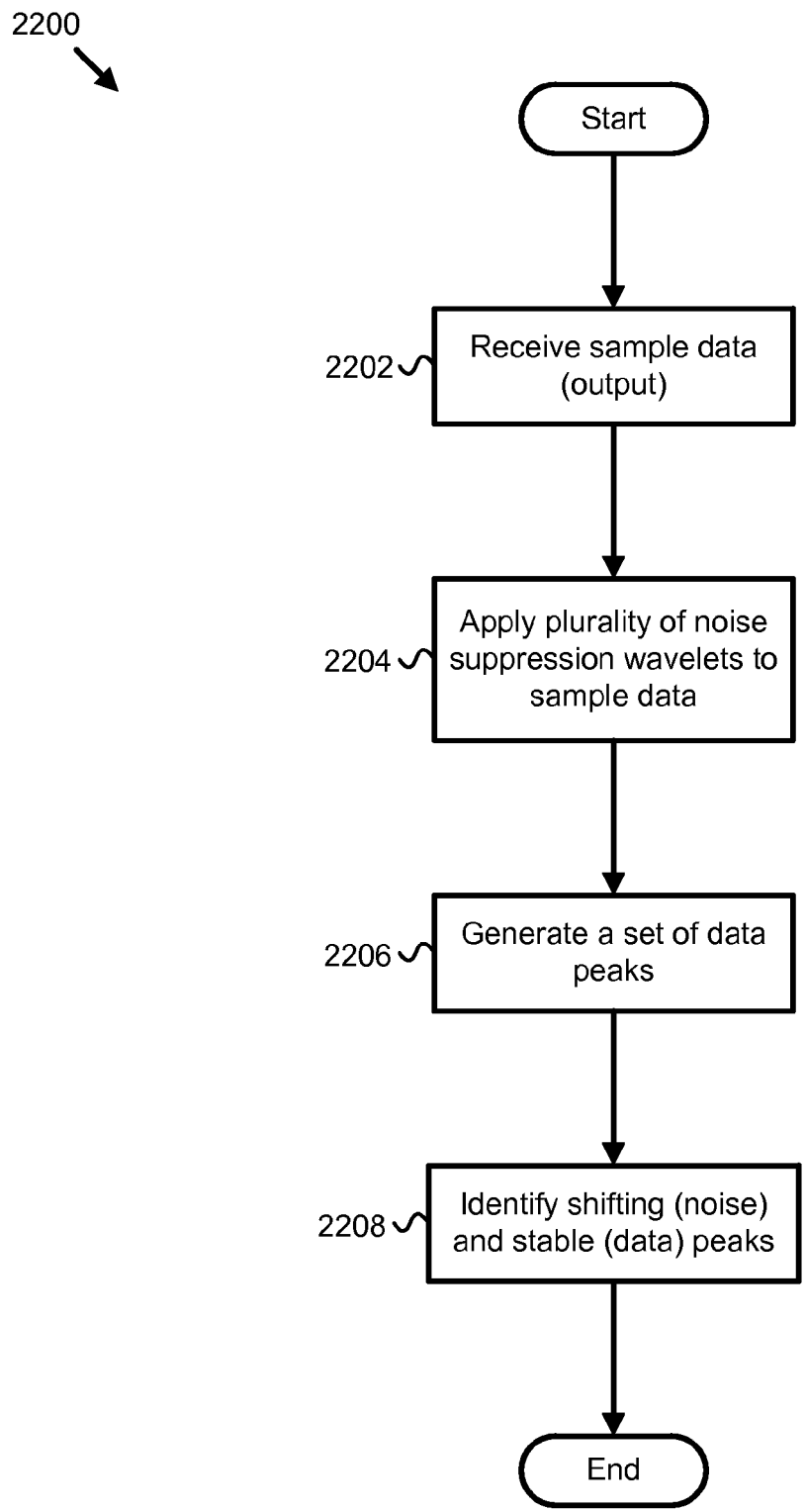
FIG. 22 is a schematic flow diagram illustrating one embodiment of a method for identifying data peaks and noise peaks in a set of sampling data in accordance with the present invention.

FIG. 22 is a schematic flow diagram illustrating one embodiment of a method 2200 for identifying data peaks and noise peaks in a set of sampling data 216 in accordance with the present invention. The method 2200 may begin with the noise filtering module 116 receiving sample data 216. The noise filtering module 116 may then apply 2204 a plurality of noise suppression wavelets 222 to the sample data 216. The noise filtering module 116 may then generate 2206 a set of data peaks, and identify 2208 shifting peaks as noise, and stable peaks as signal or data.

Figure 23:
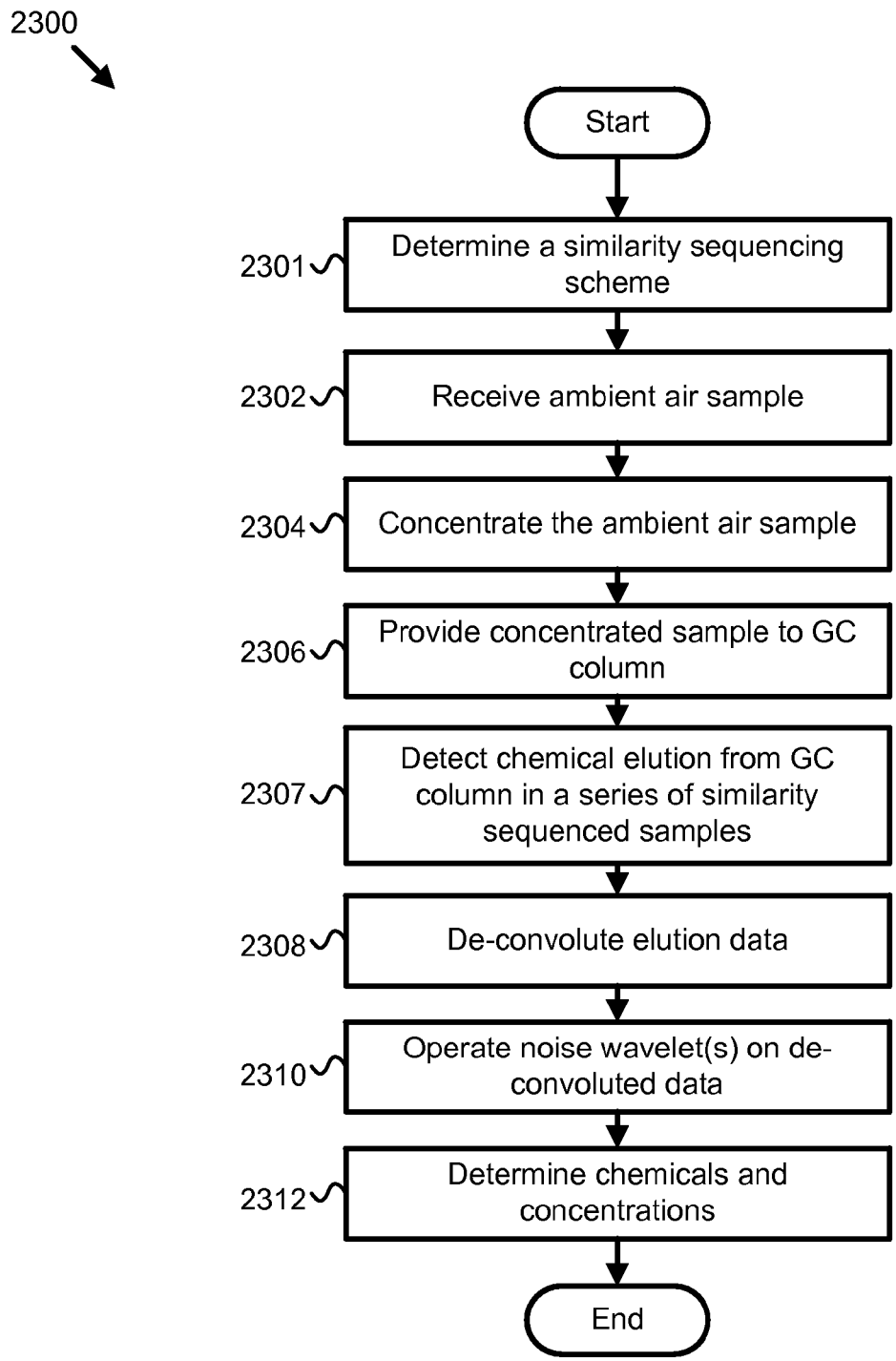
FIG. 23 is a schematic flow diagram illustrating one embodiment of a method for detecting chemicals with a GC sensor in accordance with the present invention.

FIG. 23 is a schematic flow diagram illustrating one embodiment of a method 2300 for detecting chemicals with a GC sensor in accordance with the present invention. The method includes a similarity definition module 117 determining 2301 a similarity sequencing scheme 201. The method 2300 includes a GC sensor 102 receiving 2302 an ambient air sample and a pre-concentration tube 402 concentrating 2304 the ambient air sample. The method further includes a sampling pump 806 providing 2306 the concentrated sample to at least one GC column GC1, GC2 and an elution data module 118, in one embodiment working with a similarity sequencing module 112, detecting 2307 chemical elution from the at least one GC column in a series of similarity sequenced samples (refer to the description referencing FIG. 20 for an example). The method further includes a chemical detection module 120 determining 2312 a concentration of at least one chemical in the ambient air sample based on the series of similarity sequenced samples.

In one embodiment, detecting 2307 chemical elution from the at least one GC column in a series of similarity sequenced samples includes sampling elution data from the at least one GC column GC1, GC2 in constant log-time increments. In an alternate embodiment, the method includes detecting 2307 chemical elution from the at least one GC column GC1, GC2 in a series of similarity sequenced samples by sampling elution data from the at least one GC column GC1, GC2 in constant-time increments, and transforming the constant-time increment data to constant log-time increment data.

The method 2300 includes determining a concentration of at least one chemical in the ambient air sample based on the series of similarity sequenced samples by deriving elution data from the series of similarity sequenced samples, and a signal processing module 114 de-convoluting 2308 the elution data to derive a plurality of arrival peaks 226. In one embodiment, the method includes the chemical detection module 120 checking the plurality of arrival peaks against a database of chemical signatures 234 to determine the chemicals and concentrations present 236. The method 2300 further includes determining the concentration of the at least one chemical in the ambient air sample based on an arrival time and integrated area of one of the plurality of arrival peaks 226. The method further includes determining the integrated area of one of the plurality of arrival peaks according to a rectangular approximation.

In one embodiment, the method 2300 includes de-convoluting the elution data 214 utilizing a Z-transform to de-convolute the elution data 214. Utilizing the Z-transform may include applying a Z-transform on the elution data 214 in sample space, wherein the Z-transform of an input data set is estimated to be the Z-transform of the elution data divided by a Z-transform of an estimated system 218. The Z-transform of the estimated system 218 is assumed to be constant for each of the plurality of arrival peaks.

The method may further include a noise-filtering module 116 operating 2310 at least one noise wavelet 222 on the plurality of arrival peaks 226 to determine whether each arrival peak 226 comprises one of noise 232 and data 224. In one embodiment, the method 2300 includes determining a peak 226 to be relatively stable in response to the peak reappearing after operating the at least one noise wavelet 222 within a specified range of amplitude and time values, and determining a peak 226 to be data 224 in response to determining the peak to be relatively stable. In one embodiment, the method 2300 further includes operating a set of noise wavelets 222 on the plurality of arrival peaks to determine whether each arrival peak comprises one of noise 232 and data 224. The method 2300 may further include operating a random subset of noise wavelets 230 from a set of noise wavelets 222 on the plurality of arrival peaks 226 to determine whether each arrival peak 226 comprises one of noise 232 and data 224. In one embodiment, the method 2300 further includes operating at least one primary noise wavelet 228 on the plurality of arrival peaks 226, and operating a random subset 230 of secondary noise wavelets from a set of secondary noise wavelets on the plurality of arrival peaks, to determine whether each arrival peak 226 comprises one of noise and data, in one embodiment.

Figure 24:
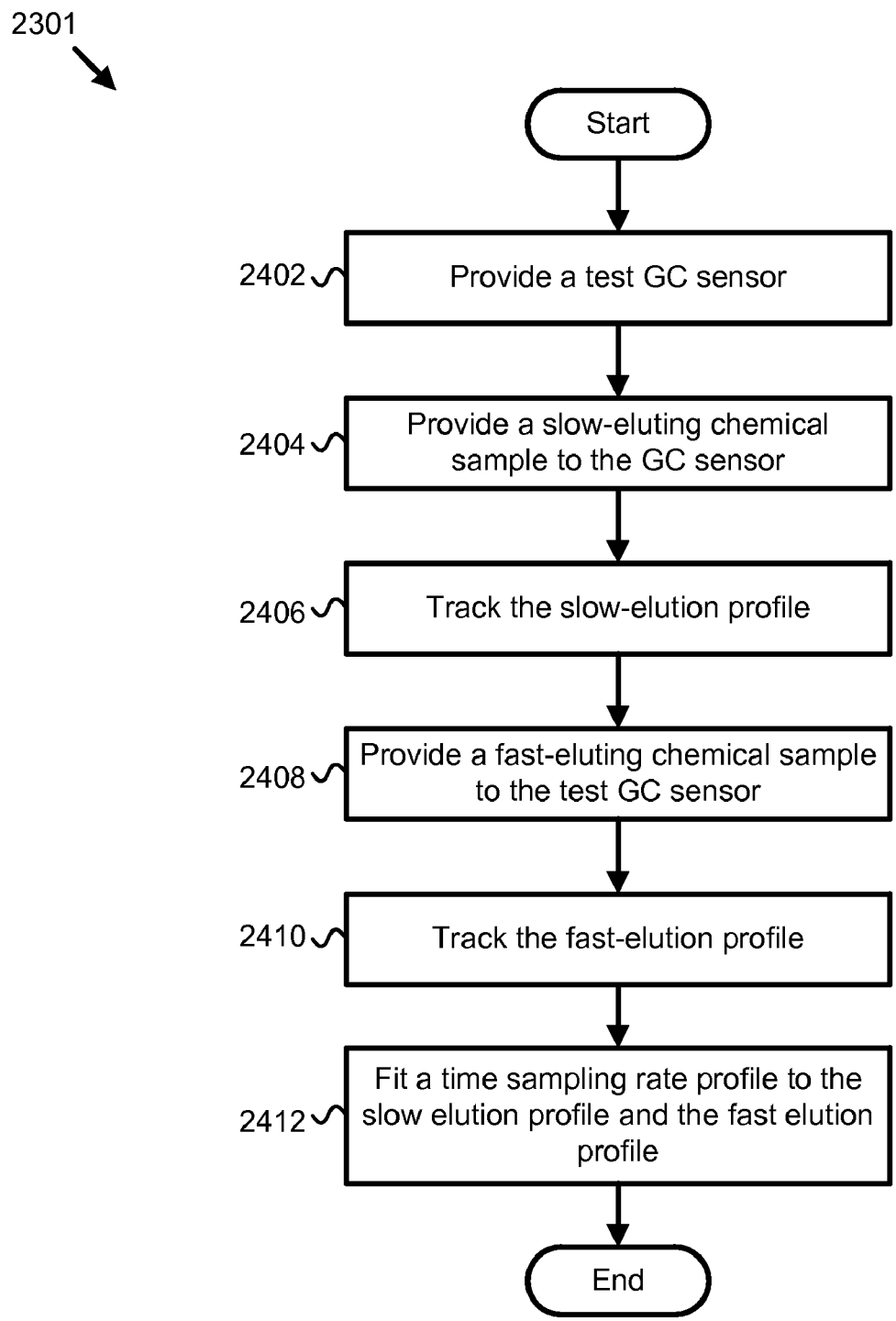
FIG. 24 is a schematic flow diagram illustrating one embodiment of determining a similarity sequencing scheme in accordance with the present invention.

FIG. 24 is a schematic flow diagram illustrating one embodiment of determining 2301 a similarity sequencing scheme 201 in accordance with the present invention. The method 2301 includes providing 2402 a test GC sensor, providing 2404 a slow-eluting chemical sample to the GC sensor, and tracking 2406 the slow-elution profile. The method 2301 further includes providing 2408 a fast-eluting chemical sample to the test GC sensor and tracking 2410 the fast-elution profile. The method 2400 further includes fitting 2412 a time sampling rate profile to the slow elution profile and the fast elution profile. Fitting 2412 the time sampling rate profile comprises fitting a profile such that the slow-eluting chemical and the fast-eluting chemical exhibit similar elution peak behavior. In one embodiment, a practitioner performs the steps 2402-2412 of determining 2301 a similarity sequencing scheme 210 illustrated in FIG. 24, and the similarity definition module 117 completes determining 2301 a similarity sequencing scheme 201 by looking up data stored on the controller 104 when the GC sensor 102 is in operation.

Fitting 2412 the time sampling rate profile may include fitting a log-time sampling rate to the data, fitting a polynomial to the data such that time samples taken along the polynomial yield similar elution peak behavior for chemicals with varying elution times, or various modifications thereof. In one embodiment, the time sampling rate profile is determined using Buckinham's Π theorem, Rayleigh's Method, and/or any other data relationship determination method known in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for detecting chemicals with a gas chromatography sensor comprising:
   determining a similarity sequencing scheme for the gas chromatography sensor, wherein the similarity sequencing scheme comprises a time sampling rate profile configured such that an early-eluting chemical and a late-eluting chemical elute over a similar sampling width;
   fitting the time sampling rate profile to a slow elution profile for the early-eluting chemical and a fast elution profile for the late-eluting chemical such that the early-eluting chemical and the late-eluting chemical elute over the similar sampling width;
   receiving an ambient air sample; concentrating the ambient air sample;
   providing the concentrated sample to at least one gas chromatography (GC) column; and
   detecting chemical elution from the at least one GC column in a series of similarity sequenced samples according to the similarity sequencing scheme; and determining a concentration of at least one chemical in the ambient air sample based on the series of similarity sequenced samples.

2. The method of claim 1, wherein the similarity sequencing scheme comprises constant log-time sampling to provide the time sampling rate profile that enables the slow elution profile for the early-eluting chemical and the fast elution profile for the late-eluting chemical to enable the early-eluting chemical and the late-eluting chemical to elute over the similar sampling width.

3. The method of claim 1, wherein the similarity sequencing scheme comprises a best-fit polynomial time mapping sequence to provide the time sampling rate profile that enables the slow elution profile for the early-eluting chemical and the fast elution profile for the late-eluting chemical to enable the early-eluting chemical and the late-eluting chemical to elute over the similar sampling width.

4. The method of claim 1, wherein determining the similarity sequencing scheme comprises providing a test GC sensor, providing a slow-eluting chemical sample to the test GC sensor and tracking the slow elution profile, providing a fast-eluting chemical sample to the test GC sensor and tracking the fast elution profile, and fitting the time sampling rate profile to the slow elution profile and the fast elution profile such that the early-eluting chemical and the late-eluting chemical elute over the similar sampling width.

5. The method of claim 1, wherein detecting chemical elution from the at least one GC column in a series of similarity sequenced samples comprises sampling elution data from the at least one GC column in time steps defined by the similarity sequencing scheme.

6. The method of claim 1, wherein detecting chemical elution from the at least one GC column in a series of similarity sequenced samples comprises sampling elution data from the at least one GC column in constant-time increments, and transforming the constant-time increment data to time step data defined by the similarity sequencing scheme.

7. The method of claim 1, wherein determining a concentration of at least one chemical in the ambient air sample based on the series of similarity sequenced samples comprises deriving elution data from the series of similarity sequenced samples, and de-convoluting the elution data to derive a plurality of arrival peaks.

8. The method of claim 7, further comprising checking the plurality of arrival peaks against a database of chemical signatures.

9. The method of claim 8, further comprising determining the concentration of the at least one chemical in the ambient air sample based on an arrival time and integrated area of one of the plurality of arrival peaks.

10. The method of claim 9, further comprising determining the integrated area of one of the plurality of arrival peaks according to one of a rectangular approximation and a trapezoidal approximation.

11. The method of claim 7, wherein de-convoluting the elution data comprises utilizing a Z-transform to de-convolute the elution data.

12. The method of claim 11, wherein utilizing the Z-transform comprises a applying a Z-transform on the elution data in sample space, wherein the Z-transform of an input data set is estimated to be the Z-transform of the elution data divided by a Z-transform of an estimated system.

13. The method of claim 12, wherein the Z-transform of the estimated system is assumed to be constant for each of the plurality of arrival peaks.

14. The method of claim 7, further comprising operating at least one noise wavelet on the plurality of arrival peaks to determine whether each arrival peak comprises one of noise and data.

15. The method of claim 14, further comprising determining a peak to be relatively stable in response to the peak reappearing after operating the at least one noise wavelet within a specified range of amplitude and time values, and determining a peak to be data in response to determining the peak to be relatively stable.

16. The method of claim 7, further comprising operating a set of noise wavelets on the plurality of arrival peaks to determine whether each arrival peak comprises one of noise and data.

17. The method of claim 7, further comprising operating a random subset of noise wavelets from a set of noise wavelets on the plurality of arrival peaks to determine whether each arrival peak comprises one of noise and data.

18. The method of claim 7, further comprising operating at least one primary noise wavelet on the plurality of arrival peaks, and operating a random subset of secondary noise wavelets from a set of secondary noise wavelets on the plurality of arrival peaks, to determine whether each arrival peak comprises one of noise and data.

19. An apparatus for detecting chemicals with a gas chromatography sensor, the apparatus comprising:
   a similarity definition module configured to determine a similarity sequencing scheme for the gas chromatography sensor, wherein the similarity sequencing scheme comprises fitting a time sampling rate profile to a slow elution profile for an early-eluting chemical and a fast elution profile for a late-eluting chemical such that the early-eluting chemical and the late-eluting chemical elute over a similar sampling width;
   an elution data module configured to interpret elution data signals from at least one gas chromatography (GC) column;
   a similarity sequencing module configured to sort the elution data signals into a series of similarity sequenced samples based on the similarity sequencing scheme; and
   a chemical detection module configured to determine a concentration of at least one chemical in the ambient air sample based on the series of similarity sequenced samples.

20. The apparatus of claim 19, further comprising a signal processing module configured to de-convolute the series of similarity sequenced samples to determine a plurality of arrival peaks, and a noise-filtering module configured to operate at least one noise wavelet on the plurality of arrival peaks to determine whether each arrival peak comprises one of noise and data.

21. The apparatus of claim 20, wherein the noise-filtering module is further configured to operate a subset of noise wavelets from a set of noise wavelets on the plurality of arrival peaks to determine whether each arrival peak comprises one of noise and data.

22. The apparatus of claim 20, wherein the signal processing module is further configured to de-convolute the series of similarity sequenced samples utilizing a modified Z-transform.

23. A system for detecting chemicals with a gas chromatography sensor, the system comprising:
   a gas chromatography (GC) sensor comprising dual GC columns;
   a controller comprising:
      a similarity definition module configured to determine a similarity sequencing scheme for the gas chromatography sensor, wherein the similarity sequencing scheme comprises fitting a time sampling rate profile to a slow elution profile for an early-eluting chemical and a fast elution profile for a late-eluting chemical such that the earl eluting chemical and the late-eluting chemical elute over a similar sampling width;
      an elution data module configured to interpret elution data signals from at least one gas chromatography (GC) column;
      a similarity sequencing module configured to sort the elution data signals into a series of similarity sequenced samples based on the similarity sequencing scheme;

a chemical detection module configured to determine a concentration of at least one chemical in the ambient air sample based on the series of similarity sequenced samples;

a signal processing module configured to de-convolute the series of similarity sequenced samples to determine a plurality of arrival peaks; and a noise-filtering module configured to operate at least one noise wavelet on the plurality of arrival peaks to determine whether each arrival peak comprises one of noise and data.

* * * * *